(12) United States Patent
Shuros et al.

(10) Patent No.: US 11,185,703 B2
(45) Date of Patent: Nov. 30, 2021

(54) LEADLESS CARDIAC PACEMAKER FOR BUNDLE OF HIS PACING

(71) Applicant: CARDIAC PACEMAKERS, INC., St. Paul, MN (US)

(72) Inventors: Allan Charles Shuros, St. Paul, MN (US); Brendan Early Koop, Ham Lake, MN (US); Keith R. Maile, New Brighton, MN (US); Brandon Christopher Fellows, Chicago, IL (US)

(73) Assignee: CARDIAC PACEMAKERS, INC.

( * ) Notice: Subject to any disclaimer, the term of this patent is extended or adjusted under 35 U.S.C. 154(b) by 410 days.

(21) Appl. No.: 16/181,943

(22) Filed: Nov. 6, 2018

(65) Prior Publication Data

US 2019/0134412 A1     May 9, 2019

Related U.S. Application Data

(60) Provisional application No. 62/582,724, filed on Nov. 7, 2017.

(51) Int. Cl.
    *A61N 1/375*      (2006.01)
    *A61N 1/378*      (2006.01)
    *A61N 1/372*      (2006.01)
    *A61N 1/36*      (2006.01)
    (Continued)

(52) U.S. Cl.
CPC ...... *A61N 1/37512* (2017.08); *A61N 1/36114* (2013.01); *A61N 1/3756* (2013.01); *A61N 1/3787* (2013.01); *A61N 1/37205* (2013.01); *A61N 1/056* (2013.01); *A61N 1/365* (2013.01); *A61N 1/37211* (2013.01); *A61N 1/37518* (2017.08)

(58) Field of Classification Search
None
See application file for complete search history.

(56) References Cited

U.S. PATENT DOCUMENTS

| | | |
|---|---|---|
| 3,835,864 A | 9/1974 | Rasor et al. |
| 3,943,936 A | 3/1976 | Rasor et al. |
| 4,142,530 A | 3/1979 | Wittkampf |

(Continued)

FOREIGN PATENT DOCUMENTS

| | | |
|---|---|---|
| AU | 2008279789 B2 | 10/2011 |
| AU | 2008329620 B2 | 5/2014 |

(Continued)

OTHER PUBLICATIONS

US 8,886,318 B2, 11/2014, Jacobson et al. (withdrawn)

(Continued)

*Primary Examiner* — Michael W Kahelin
(74) *Attorney, Agent, or Firm* — Seager, Tufte & Wickhem LLP.

(57) ABSTRACT

A leadless cardiac pacemaker (LCP) that is configured for atrial placement may include a housing, two or more electrodes and a controller that is disposed within the housing and that is operably coupled to the two or more electrodes. The controller may be configured to sense activation of the atrium of the patient's heart via two or more of the electrodes and to deliver pacing therapy via two or more of the electrodes to a ventricle of the patient's heart by pacing the bundle of His in the patient's atrioventricular septum.

17 Claims, 13 Drawing Sheets

(51) Int. Cl.
  *A61N 1/05* (2006.01)
  *A61N 1/365* (2006.01)

(56) References Cited

U.S. PATENT DOCUMENTS

| | | |
|---|---|---|
| 4,151,513 A | 4/1979 | Menken et al. |
| 4,157,720 A | 6/1979 | Greatbatch |
| RE30,366 E | 8/1980 | Rasor et al. |
| 4,243,045 A | 1/1981 | Maas |
| 4,250,884 A | 2/1981 | Hartlaub et al. |
| 4,256,115 A | 3/1981 | Bilitch |
| 4,263,919 A | 4/1981 | Levin |
| 4,310,000 A | 1/1982 | Lindemans |
| 4,312,354 A | 1/1982 | Walters |
| 4,323,081 A | 4/1982 | Wiebusch |
| 4,357,946 A | 11/1982 | Dutcher et al. |
| 4,365,639 A | 12/1982 | Goldreyer |
| 4,440,173 A | 4/1984 | Hudziak et al. |
| 4,476,868 A | 10/1984 | Thompson |
| 4,522,208 A | 6/1985 | Buffet |
| 4,537,200 A | 8/1985 | Widrow |
| 4,556,063 A | 12/1985 | Thompson et al. |
| 4,562,841 A | 1/1986 | Brockway et al. |
| 4,593,702 A | 6/1986 | Kepski et al. |
| 4,593,955 A | 6/1986 | Leiber |
| 4,630,611 A | 12/1986 | King |
| 4,635,639 A | 1/1987 | Hakala et al. |
| 4,674,508 A | 6/1987 | DeCote |
| 4,712,554 A | 12/1987 | Garson |
| 4,729,376 A | 3/1988 | DeCote |
| 4,754,753 A | 7/1988 | King |
| 4,759,366 A | 7/1988 | Callaghan |
| 4,776,338 A | 10/1988 | Lekholm et al. |
| 4,787,389 A | 11/1988 | Tarjan |
| 4,793,353 A | 12/1988 | Borkan |
| 4,819,662 A | 4/1989 | Heil et al. |
| 4,858,610 A | 8/1989 | Callaghan et al. |
| 4,886,064 A | 12/1989 | Strandberg |
| 4,887,609 A | 12/1989 | Cole |
| 4,928,688 A | 5/1990 | Mower |
| 4,967,746 A | 11/1990 | Vandegriff |
| 4,987,897 A | 1/1991 | Funke |
| 4,989,602 A | 2/1991 | Sholder et al. |
| 5,012,806 A | 5/1991 | De Bellis |
| 5,036,849 A | 8/1991 | Hauck et al. |
| 5,040,534 A | 8/1991 | Mann et al. |
| 5,058,581 A | 10/1991 | Silvian |
| 5,078,134 A | 1/1992 | Heilman et al. |
| 5,109,845 A | 5/1992 | Yuuchi et al. |
| 5,113,859 A | 5/1992 | Funke |
| 5,113,869 A | 5/1992 | Nappholz et al. |
| 5,117,824 A | 6/1992 | Keimel et al. |
| 5,127,401 A | 7/1992 | Grevious et al. |
| 5,133,353 A | 7/1992 | Hauser |
| 5,144,950 A | 9/1992 | Stoop et al. |
| 5,170,784 A | 12/1992 | Ramon et al. |
| 5,179,945 A | 1/1993 | Van Hofwegen et al. |
| 5,193,539 A | 3/1993 | Schulman et al. |
| 5,193,540 A | 3/1993 | Schulman et al. |
| 5,238,004 A | 8/1993 | Sahatjian et al. |
| 5,241,961 A | 9/1993 | Henry |
| 5,243,977 A | 9/1993 | Trabucco et al. |
| 5,259,387 A | 11/1993 | DePinto |
| 5,269,326 A | 12/1993 | Verrier |
| 5,284,136 A | 2/1994 | Hauck et al. |
| 5,300,107 A | 4/1994 | Stokes et al. |
| 5,301,677 A | 4/1994 | Hsung |
| 5,305,760 A | 4/1994 | McKown et al. |
| 5,312,439 A | 5/1994 | Loeb |
| 5,313,953 A | 5/1994 | Yomtov et al. |
| 5,314,459 A | 5/1994 | Swanson et al. |
| 5,318,597 A | 6/1994 | Hauck et al. |
| 5,324,316 A | 6/1994 | Schulman et al. |
| 5,331,966 A | 7/1994 | Bennett et al. |
| 5,334,222 A | 8/1994 | Salo et al. |
| 5,342,408 A | 8/1994 | deCoriolis et al. |
| 5,370,667 A | 12/1994 | Alt |
| 5,372,606 A | 12/1994 | Lang et al. |
| 5,376,106 A | 12/1994 | Stahmann et al. |
| 5,383,915 A | 1/1995 | Adams |
| 5,388,578 A | 2/1995 | Yomtov et al. |
| 5,404,877 A | 4/1995 | Nolan et al. |
| 5,405,367 A | 4/1995 | Schulman et al. |
| 5,411,031 A | 5/1995 | Yomtov |
| 5,411,525 A | 5/1995 | Swanson et al. |
| 5,411,535 A | 5/1995 | Fujii et al. |
| 5,456,691 A | 10/1995 | Snell |
| 5,458,622 A | 10/1995 | Alt |
| 5,466,246 A | 11/1995 | Silvian |
| 5,468,254 A | 11/1995 | Hahn et al. |
| 5,472,453 A | 12/1995 | Alt |
| 5,522,866 A | 6/1996 | Fernald |
| 5,540,727 A | 7/1996 | Tockman et al. |
| 5,545,186 A | 8/1996 | Olson et al. |
| 5,545,202 A | 8/1996 | Dahl et al. |
| 5,571,146 A | 11/1996 | Jones et al. |
| 5,591,214 A | 1/1997 | Lu |
| 5,620,466 A | 4/1997 | Haefner et al. |
| 5,634,938 A | 6/1997 | Swanson et al. |
| 5,649,968 A | 7/1997 | Alt et al. |
| 5,662,688 A | 9/1997 | Haefner et al. |
| 5,674,259 A | 10/1997 | Gray |
| 5,683,426 A | 11/1997 | Greenhut et al. |
| 5,683,432 A | 11/1997 | Goedeke et al. |
| 5,706,823 A | 1/1998 | Wodlinger |
| 5,709,215 A | 1/1998 | Perttu et al. |
| 5,720,770 A | 2/1998 | Nappholz et al. |
| 5,728,154 A | 3/1998 | Crossett et al. |
| 5,741,314 A | 4/1998 | Daly et al. |
| 5,741,315 A | 4/1998 | Lee et al. |
| 5,752,976 A | 5/1998 | Duffin et al. |
| 5,752,977 A | 5/1998 | Grevious et al. |
| 5,755,736 A | 5/1998 | Gillberg et al. |
| 5,759,199 A | 6/1998 | Snell et al. |
| 5,774,501 A | 6/1998 | Halpern et al. |
| 5,792,195 A | 8/1998 | Carlson et al. |
| 5,792,202 A | 8/1998 | Rueter |
| 5,792,203 A | 8/1998 | Schroeppel |
| 5,792,205 A | 8/1998 | Alt et al. |
| 5,792,208 A | 8/1998 | Gray |
| 5,814,089 A | 9/1998 | Stokes et al. |
| 5,827,216 A | 10/1998 | Igo et al. |
| 5,836,985 A | 11/1998 | Rostami et al. |
| 5,836,987 A | 11/1998 | Baumann et al. |
| 5,842,977 A | 12/1998 | Lesho et al. |
| 5,855,593 A | 1/1999 | Olson et al. |
| 5,873,894 A | 2/1999 | Vandegriff et al. |
| 5,891,184 A | 4/1999 | Lee et al. |
| 5,897,586 A | 4/1999 | Molina |
| 5,899,876 A | 5/1999 | Flower |
| 5,899,928 A | 5/1999 | Sholder et al. |
| 5,919,214 A | 7/1999 | Ciciarelli et al. |
| 5,935,078 A | 8/1999 | Feierbach |
| 5,941,906 A | 8/1999 | Barreras, Sr. et al. |
| 5,944,744 A | 8/1999 | Paul et al. |
| 5,954,757 A | 9/1999 | Gray |
| 5,978,713 A | 11/1999 | Prutchi et al. |
| 5,991,660 A | 11/1999 | Goyal |
| 5,991,661 A | 11/1999 | Park et al. |
| 5,999,848 A | 12/1999 | Gord et al. |
| 5,999,857 A | 12/1999 | Weijand et al. |
| 6,016,445 A | 1/2000 | Baura |
| 6,026,320 A | 2/2000 | Carlson et al. |
| 6,029,085 A | 2/2000 | Olson et al. |
| 6,041,250 A | 3/2000 | DePinto |
| 6,044,298 A | 3/2000 | Salo et al. |
| 6,044,300 A | 3/2000 | Gray |
| 6,055,454 A | 4/2000 | Heemels |
| 6,073,050 A | 6/2000 | Griffith |
| 6,076,016 A | 6/2000 | Feierbach |
| 6,077,236 A | 6/2000 | Cunningham |
| 6,080,187 A | 6/2000 | Alt et al. |
| 6,083,248 A | 7/2000 | Thompson |
| 6,106,551 A | 8/2000 | Crossett et al. |

(56) References Cited

U.S. PATENT DOCUMENTS

| | | |
|---|---|---|
| 6,115,636 A | 9/2000 | Ryan |
| 6,128,526 A | 10/2000 | Stadler et al. |
| 6,141,581 A | 10/2000 | Olson et al. |
| 6,141,588 A | 10/2000 | Cox et al. |
| 6,141,592 A | 10/2000 | Pauly |
| 6,144,879 A | 11/2000 | Gray |
| 6,162,195 A | 12/2000 | Igo et al. |
| 6,164,284 A | 12/2000 | Schulman et al. |
| 6,167,310 A | 12/2000 | Grevious |
| 6,201,993 B1 | 3/2001 | Kruse et al. |
| 6,208,894 B1 | 3/2001 | Schulman et al. |
| 6,211,799 B1 | 4/2001 | Post et al. |
| 6,221,011 B1 | 4/2001 | Bardy |
| 6,240,316 B1 | 5/2001 | Richmond et al. |
| 6,240,317 B1 | 5/2001 | Villaseca et al. |
| 6,256,534 B1 | 7/2001 | Dahl |
| 6,259,947 B1 | 7/2001 | Olson et al. |
| 6,266,558 B1 | 7/2001 | Gozani et al. |
| 6,266,567 B1 | 7/2001 | Ishikawa et al. |
| 6,270,457 B1 | 8/2001 | Bardy |
| 6,272,377 B1 | 8/2001 | Sweeney et al. |
| 6,273,856 B1 | 8/2001 | Sun et al. |
| 6,277,072 B1 | 8/2001 | Bardy |
| 6,280,380 B1 | 8/2001 | Bardy |
| 6,285,907 B1 | 9/2001 | Kramer et al. |
| 6,292,698 B1 | 9/2001 | Duffin et al. |
| 6,295,473 B1 | 9/2001 | Rosar |
| 6,297,943 B1 | 10/2001 | Carson |
| 6,298,271 B1 | 10/2001 | Weijand |
| 6,307,751 B1 | 10/2001 | Bodony et al. |
| 6,312,378 B1 | 11/2001 | Bardy |
| 6,315,721 B2 | 11/2001 | Schulman et al. |
| 6,336,903 B1 | 1/2002 | Bardy |
| 6,345,202 B2 | 2/2002 | Richmond et al. |
| 6,351,667 B1 | 2/2002 | Godie |
| 6,351,669 B1 | 2/2002 | Hartley et al. |
| 6,353,759 B1 | 3/2002 | Hartley et al. |
| 6,358,203 B2 | 3/2002 | Bardy |
| 6,361,780 B1 | 3/2002 | Ley et al. |
| 6,368,284 B1 | 4/2002 | Bardy |
| 6,371,922 B1 | 4/2002 | Baumann et al. |
| 6,398,728 B1 | 6/2002 | Bardy |
| 6,400,982 B2 | 6/2002 | Sweeney et al. |
| 6,400,990 B1 | 6/2002 | Silvian |
| 6,408,208 B1 | 6/2002 | Sun |
| 6,409,674 B1 | 6/2002 | Brockway et al. |
| 6,411,848 B2 | 6/2002 | Kramer et al. |
| 6,424,865 B1 | 7/2002 | Ding |
| 6,434,429 B1 | 8/2002 | Kraus et al. |
| 6,438,410 B2 | 8/2002 | Hsu et al. |
| 6,438,417 B1 | 8/2002 | Rockwell et al. |
| 6,438,421 B1 | 8/2002 | Stahmann et al. |
| 6,440,066 B1 | 8/2002 | Bardy |
| 6,441,747 B1 | 8/2002 | Khair et al. |
| 6,442,426 B1 | 8/2002 | Kroll |
| 6,442,432 B2 | 8/2002 | Lee |
| 6,443,891 B1 | 9/2002 | Grevious |
| 6,445,953 B1 | 9/2002 | Bulkes et al. |
| 6,453,200 B1 | 9/2002 | Koslar |
| 6,459,929 B1 | 10/2002 | Hopper et al. |
| 6,470,215 B1 | 10/2002 | Kraus et al. |
| 6,471,645 B1 | 10/2002 | Warkentin et al. |
| 6,480,745 B2 | 11/2002 | Nelson et al. |
| 6,487,443 B2 | 11/2002 | Olson et al. |
| 6,490,487 B1 | 12/2002 | Kraus et al. |
| 6,498,951 B1 | 12/2002 | Larson et al. |
| 6,507,755 B1 | 1/2003 | Gozani et al. |
| 6,507,759 B1 | 1/2003 | Prutchi et al. |
| 6,508,803 B1 | 1/2003 | Horikawa et al. |
| 6,512,940 B1 | 1/2003 | Brabec et al. |
| 6,522,915 B1 | 2/2003 | Ceballos et al. |
| 6,526,311 B2 | 2/2003 | Begemann |
| 6,539,253 B2 | 3/2003 | Thompson et al. |
| 6,542,775 B2 | 4/2003 | Ding et al. |
| 6,553,258 B2 | 4/2003 | Stahmann et al. |
| 6,561,975 B1 | 5/2003 | Pool et al. |
| 6,564,807 B1 | 5/2003 | Schulman et al. |
| 6,574,506 B2 | 6/2003 | Kramer et al. |
| 6,584,351 B1 | 6/2003 | Ekwall |
| 6,584,352 B2 | 6/2003 | Combs et al. |
| 6,597,948 B1 | 7/2003 | Rockwell et al. |
| 6,597,951 B2 | 7/2003 | Kramer et al. |
| 6,622,046 B2 | 9/2003 | Fraley et al. |
| 6,628,985 B2 | 9/2003 | Sweeney et al. |
| 6,647,292 B1 | 11/2003 | Bardy et al. |
| 6,666,844 B1 | 12/2003 | Igo et al. |
| 6,689,117 B2 | 2/2004 | Sweeney et al. |
| 6,690,959 B2 | 2/2004 | Thompson |
| 6,694,189 B2 | 2/2004 | Begemann |
| 6,704,602 B2 | 3/2004 | Berg et al. |
| 6,718,212 B2 | 4/2004 | Parry et al. |
| 6,721,597 B1 | 4/2004 | Bardy et al. |
| 6,738,670 B1 | 5/2004 | Almendinger et al. |
| 6,746,797 B2 | 6/2004 | Benson et al. |
| 6,749,566 B2 | 6/2004 | Russ |
| 6,758,810 B2 | 7/2004 | Lebel et al. |
| 6,763,269 B2 | 7/2004 | Cox |
| 6,778,860 B2 | 8/2004 | Ostroff et al. |
| 6,788,971 B1 | 9/2004 | Sloman et al. |
| 6,788,974 B2 | 9/2004 | Bardy et al. |
| 6,804,558 B2 | 10/2004 | Haller et al. |
| 6,807,442 B1 | 10/2004 | Myklebust et al. |
| 6,847,844 B2 | 1/2005 | Sun et al. |
| 6,871,095 B2 | 3/2005 | Stahmann et al. |
| 6,878,112 B2 | 4/2005 | Linberg et al. |
| 6,885,889 B2 | 4/2005 | Chinchoy |
| 6,892,094 B2 | 5/2005 | Ousdigian et al. |
| 6,897,788 B2 | 5/2005 | Khair et al. |
| 6,904,315 B2 | 6/2005 | Panken et al. |
| 6,922,592 B2 | 7/2005 | Thompson et al. |
| 6,931,282 B2 | 8/2005 | Esler |
| 6,934,585 B1 | 8/2005 | Schloss et al. |
| 6,957,107 B2 | 10/2005 | Rogers et al. |
| 6,978,176 B2 | 12/2005 | Lattouf |
| 6,985,773 B2 | 1/2006 | Von Arx et al. |
| 6,990,375 B2 | 1/2006 | Kloss et al. |
| 7,001,366 B2 | 2/2006 | Ballard |
| 7,003,350 B2 | 2/2006 | Denker et al. |
| 7,006,864 B2 | 2/2006 | Echt et al. |
| 7,013,178 B2 | 3/2006 | Reinke et al. |
| 7,027,871 B2 | 4/2006 | Burnes et al. |
| 7,050,849 B2 | 5/2006 | Echt et al. |
| 7,060,031 B2 | 6/2006 | Webb et al. |
| 7,063,693 B2 | 6/2006 | Guenst |
| 7,082,336 B2 | 7/2006 | Ransbury et al. |
| 7,085,606 B2 | 8/2006 | Flach et al. |
| 7,092,758 B2 | 8/2006 | Sun et al. |
| 7,110,824 B2 | 9/2006 | Amundson et al. |
| 7,120,504 B2 | 10/2006 | Osypka |
| 7,130,681 B2 | 10/2006 | Gebhardt et al. |
| 7,139,613 B2 | 11/2006 | Reinke et al. |
| 7,142,912 B2 | 11/2006 | Wagner et al. |
| 7,146,225 B2 | 12/2006 | Guenst et al. |
| 7,146,226 B2 | 12/2006 | Lau et al. |
| 7,149,581 B2 | 12/2006 | Goedeke |
| 7,149,588 B2 | 12/2006 | Lau et al. |
| 7,158,839 B2 | 1/2007 | Lau |
| 7,162,307 B2 | 1/2007 | Patrias |
| 7,164,952 B2 | 1/2007 | Lau et al. |
| 7,177,700 B1 | 2/2007 | Cox |
| 7,181,505 B2 | 2/2007 | Haller et al. |
| 7,184,830 B2 | 2/2007 | Echt et al. |
| 7,186,214 B2 | 3/2007 | Ness |
| 7,191,015 B2 | 3/2007 | Lamson et al. |
| 7,200,437 B1 | 4/2007 | Nabutovsky et al. |
| 7,200,439 B2 | 4/2007 | Zdeblick et al. |
| 7,206,423 B1 | 4/2007 | Feng et al. |
| 7,209,785 B2 | 4/2007 | Kim et al. |
| 7,209,790 B2 | 4/2007 | Thompson et al. |
| 7,211,884 B1 | 5/2007 | Davis et al. |
| 7,212,871 B1 | 5/2007 | Morgan |
| 7,226,440 B2 | 6/2007 | Gelfand et al. |
| 7,228,183 B2 | 6/2007 | Sun et al. |
| 7,236,821 B2 | 6/2007 | Cates et al. |

(56) References Cited

U.S. PATENT DOCUMENTS

| | | |
|---|---|---|
| 7,236,829 B1 | 6/2007 | Farazi et al. |
| 7,254,448 B2 | 8/2007 | Almendinger et al. |
| 7,260,436 B2 | 8/2007 | Kilgore et al. |
| 7,270,669 B1 | 9/2007 | Sra |
| 7,272,448 B1 | 9/2007 | Morgan et al. |
| 7,277,755 B1 | 10/2007 | Falkenberg et al. |
| 7,280,872 B1 | 10/2007 | Mosesov et al. |
| 7,288,096 B2 | 10/2007 | Chin |
| 7,289,847 B1 | 10/2007 | Gill et al. |
| 7,289,852 B2 | 10/2007 | Helfinstine et al. |
| 7,289,853 B1 | 10/2007 | Campbell et al. |
| 7,289,855 B2 | 10/2007 | Nghiem et al. |
| 7,302,294 B2 | 11/2007 | Kamath et al. |
| 7,305,266 B1 | 12/2007 | Kroll |
| 7,310,556 B2 | 12/2007 | Bulkes |
| 7,319,905 B1 | 1/2008 | Morgan et al. |
| 7,321,798 B2 | 1/2008 | Muhlenberg et al. |
| 7,333,853 B2 | 2/2008 | Mazar et al. |
| 7,336,994 B2 | 2/2008 | Hettrick et al. |
| 7,347,819 B2 | 3/2008 | Lebel et al. |
| 7,366,572 B2 | 4/2008 | Heruth et al. |
| 7,373,207 B2 | 5/2008 | Lattouf |
| 7,384,403 B2 | 6/2008 | Sherman |
| 7,386,342 B1 | 6/2008 | Falkenberg et al. |
| 7,392,090 B2 | 6/2008 | Sweeney et al. |
| 7,406,105 B2 | 7/2008 | DelMain et al. |
| 7,406,349 B2 | 7/2008 | Seeberger et al. |
| 7,410,497 B2 | 8/2008 | Hastings et al. |
| 7,425,200 B2 | 9/2008 | Brockway et al. |
| 7,433,739 B1 | 10/2008 | Salys et al. |
| 7,496,409 B2 | 2/2009 | Greenhut et al. |
| 7,496,410 B2 | 2/2009 | Heil |
| 7,502,652 B2 | 3/2009 | Gaunt et al. |
| 7,512,448 B2 | 3/2009 | Malick et al. |
| 7,515,969 B2 | 4/2009 | Tockman et al. |
| 7,526,342 B2 | 4/2009 | Chin et al. |
| 7,529,589 B2 | 5/2009 | Williams et al. |
| 7,532,933 B2 | 5/2009 | Hastings et al. |
| 7,536,222 B2 | 5/2009 | Bardy et al. |
| 7,536,224 B2 | 5/2009 | Ritscher et al. |
| 7,539,541 B2 | 5/2009 | Quiles et al. |
| 7,544,197 B2 | 6/2009 | Kelsch et al. |
| 7,558,631 B2 | 7/2009 | Cowan et al. |
| 7,565,195 B1 | 7/2009 | Kroll et al. |
| 7,584,002 B2 | 9/2009 | Burnes et al. |
| 7,590,455 B2 | 9/2009 | Heruth et al. |
| 7,606,621 B2 | 10/2009 | Brisken et al. |
| 7,610,088 B2 | 10/2009 | Chinchoy |
| 7,610,092 B2 | 10/2009 | Cowan et al. |
| 7,610,099 B2 | 10/2009 | Almendinger et al. |
| 7,610,104 B2 | 10/2009 | Kaplan et al. |
| 7,616,991 B2 | 11/2009 | Mann et al. |
| 7,617,001 B2 | 11/2009 | Penner et al. |
| 7,617,007 B2 | 11/2009 | Williams et al. |
| 7,630,767 B1 | 12/2009 | Poore et al. |
| 7,634,313 B1 | 12/2009 | Kroll et al. |
| 7,637,867 B2 | 12/2009 | Zdeblick |
| 7,640,060 B2 | 12/2009 | Zdeblick |
| 7,647,109 B2 | 1/2010 | Hastings et al. |
| 7,650,186 B2 | 1/2010 | Hastings et al. |
| 7,657,311 B2 | 2/2010 | Bardy et al. |
| 7,668,596 B2 | 2/2010 | Von Arx et al. |
| 7,682,316 B2 | 3/2010 | Anderson et al. |
| 7,691,047 B2 | 4/2010 | Ferrari |
| 7,702,392 B2 | 4/2010 | Echt et al. |
| 7,713,194 B2 | 5/2010 | Zdeblick |
| 7,713,195 B2 | 5/2010 | Zdeblick |
| 7,729,783 B2 | 6/2010 | Michels et al. |
| 7,734,333 B2 | 6/2010 | Ghanem et al. |
| 7,734,343 B2 | 6/2010 | Ransbury et al. |
| 7,738,958 B2 | 6/2010 | Zdeblick et al. |
| 7,738,964 B2 | 6/2010 | Von Arx et al. |
| 7,742,812 B2 | 6/2010 | Ghanem et al. |
| 7,742,816 B2 | 6/2010 | Masoud et al. |
| 7,742,822 B2 | 6/2010 | Masoud et al. |
| 7,743,151 B2 | 6/2010 | Vallapureddy et al. |
| 7,747,335 B2 | 6/2010 | Williams |
| 7,751,881 B2 | 7/2010 | Cowan et al. |
| 7,758,521 B2 | 7/2010 | Morris et al. |
| 7,761,150 B2 | 7/2010 | Ghanem et al. |
| 7,761,164 B2 | 7/2010 | Verhoef et al. |
| 7,765,001 B2 | 7/2010 | Echt et al. |
| 7,769,452 B2 | 8/2010 | Ghanem et al. |
| 7,783,362 B2 | 8/2010 | Whitehurst et al. |
| 7,792,588 B2 | 9/2010 | Harding |
| 7,797,059 B1 | 9/2010 | Bomzin et al. |
| 7,801,596 B2 | 9/2010 | Fischell et al. |
| 7,809,438 B2 | 10/2010 | Echt et al. |
| 7,840,281 B2 | 11/2010 | Kveen et al. |
| 7,844,331 B2 | 11/2010 | Li et al. |
| 7,844,348 B2 | 11/2010 | Swoyer et al. |
| 7,846,088 B2 | 12/2010 | Ness |
| 7,848,815 B2 | 12/2010 | Brisken et al. |
| 7,848,823 B2 | 12/2010 | Drasler et al. |
| 7,860,455 B2 | 12/2010 | Fukumoto et al. |
| 7,871,433 B2 | 1/2011 | Lattouf |
| 7,877,136 B1 | 1/2011 | Moffitt et al. |
| 7,877,142 B2 | 1/2011 | Moaddeb et al. |
| 7,881,786 B2 | 2/2011 | Jackson |
| 7,881,798 B2 | 2/2011 | Miesel et al. |
| 7,881,810 B1 | 2/2011 | Chitre et al. |
| 7,890,173 B2 | 2/2011 | Brisken et al. |
| 7,890,181 B2 | 2/2011 | Denzene et al. |
| 7,890,192 B1 | 2/2011 | Kelsch et al. |
| 7,894,885 B2 | 2/2011 | Bartal et al. |
| 7,894,894 B2 | 2/2011 | Stadler et al. |
| 7,894,907 B2 | 2/2011 | Cowan et al. |
| 7,894,910 B2 | 2/2011 | Cowan et al. |
| 7,894,915 B1 | 2/2011 | Chitre et al. |
| 7,899,537 B1 | 3/2011 | Kroll et al. |
| 7,899,541 B2 | 3/2011 | Cowan et al. |
| 7,899,542 B2 | 3/2011 | Cowan et al. |
| 7,899,554 B2 | 3/2011 | Williams et al. |
| 7,901,360 B1 | 3/2011 | Yang et al. |
| 7,904,170 B2 | 3/2011 | Harding |
| 7,907,993 B2 | 3/2011 | Ghanem et al. |
| 7,920,928 B1 | 4/2011 | Fang et al. |
| 7,925,343 B1 | 4/2011 | Min et al. |
| 7,930,022 B2 | 4/2011 | Zhang et al. |
| 7,930,040 B1 | 4/2011 | Kelsch et al. |
| 7,937,135 B2 | 5/2011 | Ghanem et al. |
| 7,937,148 B2 | 5/2011 | Jacobson |
| 7,937,161 B2 | 5/2011 | Hastings et al. |
| 7,941,214 B2 | 5/2011 | Kleckner et al. |
| 7,945,333 B2 | 5/2011 | Jacobson |
| 7,946,997 B2 | 5/2011 | Hübinette |
| 7,949,404 B2 | 5/2011 | Hill |
| 7,949,405 B2 | 5/2011 | Feher |
| 7,953,486 B2 | 5/2011 | Daum et al. |
| 7,953,493 B2 | 5/2011 | Fowler et al. |
| 7,962,202 B2 | 6/2011 | Bhunia |
| 7,974,702 B1 | 7/2011 | Fain et al. |
| 7,979,136 B2 | 7/2011 | Young et al. |
| 7,983,753 B2 | 7/2011 | Severin |
| 7,991,467 B2 | 8/2011 | Markowitz et al. |
| 7,991,471 B2 | 8/2011 | Ghanem et al. |
| 7,996,087 B2 | 8/2011 | Cowan et al. |
| 8,000,791 B2 | 8/2011 | Sunagawa et al. |
| 8,000,807 B2 | 8/2011 | Morris et al. |
| 8,001,975 B2 | 8/2011 | DiSilvestro et al. |
| 8,002,700 B2 | 8/2011 | Ferek-Petric et al. |
| 8,010,209 B2 | 8/2011 | Jacobson |
| 8,019,419 B1 | 9/2011 | Panescu et al. |
| 8,019,434 B2 | 9/2011 | Quiles et al. |
| 8,027,727 B2 | 9/2011 | Freeberg |
| 8,027,729 B2 | 9/2011 | Sunagawa et al. |
| 8,032,219 B2 | 10/2011 | Neumann et al. |
| 8,036,743 B2 | 10/2011 | Savage et al. |
| 8,046,079 B2 | 10/2011 | Bange et al. |
| 8,046,080 B2 | 10/2011 | Von Arx et al. |
| 8,050,297 B2 | 11/2011 | DelMain et al. |
| 8,050,759 B2 | 11/2011 | Stegemann et al. |
| 8,050,774 B2 | 11/2011 | Kveen et al. |
| 8,055,345 B2 | 11/2011 | Li et al. |

(56) References Cited

U.S. PATENT DOCUMENTS

| | | |
|---|---|---|
| 8,055,350 B2 | 11/2011 | Roberts |
| 8,060,212 B1 | 11/2011 | Rios et al. |
| 8,065,018 B2 | 11/2011 | Haubrich et al. |
| 8,073,542 B2 | 12/2011 | Doerr |
| 8,078,278 B2 | 12/2011 | Penner |
| 8,078,283 B2 | 12/2011 | Cowan et al. |
| 8,095,123 B2 | 1/2012 | Gray |
| 8,102,789 B2 | 1/2012 | Rosar et al. |
| 8,103,359 B2 | 1/2012 | Reddy |
| 8,103,361 B2 | 1/2012 | Moser |
| 8,112,148 B2 | 2/2012 | Giftakis et al. |
| 8,114,021 B2 | 2/2012 | Robertson et al. |
| 8,121,680 B2 | 2/2012 | Falkenberg et al. |
| 8,123,684 B2 | 2/2012 | Zdeblick |
| 8,126,545 B2 | 2/2012 | Flach et al. |
| 8,131,334 B2 | 3/2012 | Lu et al. |
| 8,140,161 B2 | 3/2012 | Willerton et al. |
| 8,150,521 B2 | 4/2012 | Crowley et al. |
| 8,160,672 B2 | 4/2012 | Kim et al. |
| 8,160,702 B2 | 4/2012 | Mann et al. |
| 8,160,704 B2 | 4/2012 | Freeberg |
| 8,165,694 B2 | 4/2012 | Carbanaru et al. |
| 8,175,715 B1 | 5/2012 | Cox |
| 8,180,451 B2 | 5/2012 | Hickman et al. |
| 8,185,213 B2 | 5/2012 | Kveen et al. |
| 8,187,161 B2 | 5/2012 | Li et al. |
| 8,195,293 B2 | 6/2012 | Limousin et al. |
| 8,204,595 B2 | 6/2012 | Pianca et al. |
| 8,204,605 B2 | 6/2012 | Hastings et al. |
| 8,209,014 B2 | 6/2012 | Doerr |
| 8,214,043 B2 | 7/2012 | Matos |
| 8,224,244 B2 | 7/2012 | Kim et al. |
| 8,229,556 B2 | 7/2012 | Li |
| 8,233,985 B2 | 7/2012 | Bulkes et al. |
| 8,262,578 B1 | 9/2012 | Bharmi et al. |
| 8,265,748 B2 | 9/2012 | Liu et al. |
| 8,265,757 B2 | 9/2012 | Mass et al. |
| 8,280,521 B2 | 10/2012 | Haubrich et al. |
| 8,285,387 B2 | 10/2012 | Utsi et al. |
| 8,290,598 B2 | 10/2012 | Boon et al. |
| 8,290,600 B2 | 10/2012 | Hastings et al. |
| 8,295,939 B2 | 10/2012 | Jacobson |
| 8,301,254 B2 | 10/2012 | Mosesov et al. |
| 8,315,701 B2 | 11/2012 | Cowan et al. |
| 8,315,708 B2 | 11/2012 | Berthelsdorf et al. |
| 8,321,021 B2 | 11/2012 | Kisker et al. |
| 8,321,036 B2 | 11/2012 | Brockway et al. |
| 8,332,036 B2 | 12/2012 | Hastings et al. |
| 8,335,563 B2 | 12/2012 | Stessman |
| 8,335,568 B2 | 12/2012 | Heruth et al. |
| 8,340,750 B2 | 12/2012 | Prakash et al. |
| 8,340,780 B2 | 12/2012 | Hastings et al. |
| 8,352,025 B2 | 1/2013 | Jacobson |
| 8,352,028 B2 | 1/2013 | Wenger |
| 8,352,038 B2 | 1/2013 | Mao et al. |
| 8,359,098 B2 | 1/2013 | Lund et al. |
| 8,364,261 B2 | 1/2013 | Stubbs et al. |
| 8,364,276 B2 | 1/2013 | Willis |
| 8,369,959 B2 | 2/2013 | Meskens |
| 8,369,962 B2 | 2/2013 | Abrahamson |
| 8,380,320 B2 | 2/2013 | Spital |
| 8,386,051 B2 | 2/2013 | Rys |
| 8,391,981 B2 | 3/2013 | Mosesov |
| 8,391,990 B2 | 3/2013 | Smith et al. |
| 8,406,874 B2 | 3/2013 | Liu et al. |
| 8,406,879 B2 | 3/2013 | Shuros et al. |
| 8,406,886 B2 | 3/2013 | Gaunt et al. |
| 8,412,352 B2 | 4/2013 | Griswold et al. |
| 8,417,340 B2 | 4/2013 | Goossen |
| 8,417,341 B2 | 4/2013 | Freeberg |
| 8,423,149 B2 | 4/2013 | Hennig |
| 8,428,722 B2 | 4/2013 | Verhoef et al. |
| 8,433,402 B2 | 4/2013 | Ruben et al. |
| 8,433,409 B2 | 4/2013 | Johnson et al. |
| 8,433,420 B2 | 4/2013 | Bange et al. |
| 8,447,412 B2 | 5/2013 | Dal Molin et al. |
| 8,452,413 B2 | 5/2013 | Young et al. |
| 8,457,740 B2 | 6/2013 | Osche |
| 8,457,742 B2 | 6/2013 | Jacobson |
| 8,457,744 B2 | 6/2013 | Janzig et al. |
| 8,457,761 B2 | 6/2013 | Wariar |
| 8,478,407 B2 | 7/2013 | Demmer et al. |
| 8,478,408 B2 | 7/2013 | Hastings et al. |
| 8,478,431 B2 | 7/2013 | Griswold et al. |
| 8,494,632 B2 | 7/2013 | Sun et al. |
| 8,504,156 B2 | 8/2013 | Bonner et al. |
| 8,509,910 B2 | 8/2013 | Sowder et al. |
| 8,515,559 B2 | 8/2013 | Roberts et al. |
| 8,525,340 B2 | 9/2013 | Eckhardt et al. |
| 8,527,068 B2 | 9/2013 | Ostroff |
| 8,532,790 B2 | 9/2013 | Griswold |
| 8,538,526 B2 | 9/2013 | Stahmann et al. |
| 8,541,131 B2 | 9/2013 | Lund et al. |
| 8,543,205 B2 | 9/2013 | Ostroff |
| 8,547,248 B2 | 10/2013 | Zdeblick et al. |
| 8,548,605 B2 | 10/2013 | Ollivier |
| 8,554,333 B2 | 10/2013 | Wu et al. |
| 8,565,882 B2 | 10/2013 | Matos |
| 8,565,897 B2 | 10/2013 | Regnier et al. |
| 8,571,678 B2 | 10/2013 | Wang |
| 8,577,327 B2 | 11/2013 | Makdissi et al. |
| 8,588,926 B2 | 11/2013 | Moore et al. |
| 8,612,002 B2 | 12/2013 | Faltys et al. |
| 8,615,310 B2 | 12/2013 | Khairkhahan et al. |
| 8,626,280 B2 | 1/2014 | Allavatam et al. |
| 8,626,294 B2 | 1/2014 | Sheldon et al. |
| 8,634,908 B2 | 1/2014 | Cowan |
| 8,634,912 B2 | 1/2014 | Bornzin et al. |
| 8,634,919 B1 | 1/2014 | Hou et al. |
| 8,639,335 B2 | 1/2014 | Peichel et al. |
| 8,644,934 B2 | 2/2014 | Hastings et al. |
| 8,649,859 B2 | 2/2014 | Smith et al. |
| 8,670,842 B1 | 3/2014 | Bornzin et al. |
| 8,676,319 B2 | 3/2014 | Knoll |
| 8,676,335 B2 | 3/2014 | Katoozi et al. |
| 8,700,173 B2 | 4/2014 | Edlund |
| 8,700,181 B2 | 4/2014 | Bornzin et al. |
| 8,705,599 B2 | 4/2014 | dal Molin et al. |
| 8,718,766 B2 | 5/2014 | Wahlberg |
| 8,718,773 B2 | 5/2014 | Willis et al. |
| 8,725,260 B2 | 5/2014 | Shuros et al. |
| 8,738,133 B2 | 5/2014 | Shuros et al. |
| 8,738,147 B2 | 5/2014 | Hastings et al. |
| 8,744,555 B2 | 6/2014 | Allavatam et al. |
| 8,744,572 B1 | 6/2014 | Greenhut et al. |
| 8,747,314 B2 | 6/2014 | Stahmann et al. |
| 8,755,884 B2 | 6/2014 | Demmer et al. |
| 8,758,365 B2 | 6/2014 | Bonner et al. |
| 8,768,483 B2 | 7/2014 | Schmitt et al. |
| 8,774,572 B2 | 7/2014 | Hamamoto |
| 8,781,605 B2 | 7/2014 | Bornzin et al. |
| 8,788,035 B2 | 7/2014 | Jacobson |
| 8,788,053 B2 | 7/2014 | Jacobson |
| 8,798,740 B2 | 8/2014 | Samade et al. |
| 8,798,745 B2 | 8/2014 | Jacobson |
| 8,798,762 B2 | 8/2014 | Fain et al. |
| 8,798,770 B2 | 8/2014 | Reddy |
| 8,805,505 B1 | 8/2014 | Roberts |
| 8,805,528 B2 | 8/2014 | Corndorf |
| 8,812,109 B2 | 8/2014 | Blomqvist et al. |
| 8,818,504 B2 | 8/2014 | Bodner et al. |
| 8,827,913 B2 | 9/2014 | Havel et al. |
| 8,831,747 B1 | 9/2014 | Min et al. |
| 8,855,789 B2 | 10/2014 | Jacobson |
| 8,864,676 B2 | 10/2014 | Beasley et al. |
| 8,868,186 B2 | 10/2014 | Kroll |
| 8,886,339 B2 | 11/2014 | Faltys et al. |
| 8,888,709 B2 | 11/2014 | Shuros et al. |
| 8,903,473 B2 | 12/2014 | Rogers et al. |
| 8,903,500 B2 | 12/2014 | Smith et al. |
| 8,903,513 B2 | 12/2014 | Ollivier |
| 8,909,336 B2 | 12/2014 | Navarro-Paredes et al. |
| 8,914,131 B2 | 12/2014 | Bornzin et al. |
| 8,923,795 B2 | 12/2014 | Makdissi et al. |

(56) References Cited

U.S. PATENT DOCUMENTS

| | | |
|---|---|---|
| 8,923,963 B2 | 12/2014 | Bonner et al. |
| 8,938,300 B2 | 1/2015 | Rosero |
| 8,942,806 B2 | 1/2015 | Sheldon et al. |
| 8,958,892 B2 | 2/2015 | Khairkhahan et al. |
| 8,977,358 B2 | 3/2015 | Ewert et al. |
| 8,989,873 B2 | 3/2015 | Locsin |
| 8,996,109 B2 | 3/2015 | Karst et al. |
| 9,002,467 B2 | 4/2015 | Smith et al. |
| 9,008,776 B2 | 4/2015 | Cowan et al. |
| 9,008,777 B2 | 4/2015 | Dianaty et al. |
| 9,014,818 B2 | 4/2015 | Deterre et al. |
| 9,017,341 B2 | 4/2015 | Bornzin et al. |
| 9,020,611 B2 | 4/2015 | Khairkhahan et al. |
| 9,037,262 B2 | 5/2015 | Regnier et al. |
| 9,042,984 B2 | 5/2015 | Demmer et al. |
| 9,072,911 B2 | 7/2015 | Hastings et al. |
| 9,072,913 B2 | 7/2015 | Jacobson |
| 9,155,882 B2 | 10/2015 | Grubac et al. |
| 9,168,372 B2 | 10/2015 | Fain |
| 9,168,380 B1 | 10/2015 | Greenhut et al. |
| 9,168,383 B2 | 10/2015 | Jacobson et al. |
| 9,180,285 B2 | 11/2015 | Moore et al. |
| 9,192,774 B2 | 11/2015 | Jacobson |
| 9,205,225 B2 | 12/2015 | Khairkhahan et al. |
| 9,216,285 B1 | 12/2015 | Boling et al. |
| 9,216,293 B2 | 12/2015 | Berthiaume et al. |
| 9,216,298 B2 | 12/2015 | Jacobson |
| 9,227,077 B2 | 1/2016 | Jacobson |
| 9,238,145 B2 | 1/2016 | Wenzel et al. |
| 9,242,102 B2 | 1/2016 | Khairkhahan et al. |
| 9,242,113 B2 | 1/2016 | Smith et al. |
| 9,248,300 B2 | 2/2016 | Rys et al. |
| 9,265,436 B2 | 2/2016 | Min et al. |
| 9,265,962 B2 | 2/2016 | Dianaty et al. |
| 9,272,155 B2 | 3/2016 | Ostroff |
| 9,278,218 B2 | 3/2016 | Karst et al. |
| 9,278,229 B1 | 3/2016 | Reinke et al. |
| 9,283,381 B2 | 3/2016 | Grubac et al. |
| 9,283,382 B2 | 3/2016 | Berthiaume et al. |
| 9,289,612 B1 | 3/2016 | Sambelashvili et al. |
| 9,302,115 B2 | 4/2016 | Molin et al. |
| 9,333,364 B2 | 5/2016 | Echt et al. |
| 9,351,648 B2 | 5/2016 | Mothilal et al. |
| 9,358,387 B2 | 6/2016 | Suwito et al. |
| 9,358,400 B2 | 6/2016 | Jacobson |
| 9,364,675 B2 | 6/2016 | Deterre et al. |
| 9,370,663 B2 | 6/2016 | Moulder |
| 9,375,580 B2 | 6/2016 | Bonner et al. |
| 9,375,581 B2 | 6/2016 | Baru et al. |
| 9,381,365 B2 | 7/2016 | Kibler et al. |
| 9,393,424 B2 | 7/2016 | Demmer et al. |
| 9,393,436 B2 | 7/2016 | Doerr |
| 9,399,139 B2 | 7/2016 | Demmer et al. |
| 9,399,140 B2 | 7/2016 | Cho et al. |
| 9,409,033 B2 | 8/2016 | Jacobson |
| 9,427,594 B1 | 8/2016 | Bornzin et al. |
| 9,433,368 B2 | 9/2016 | Stahmann et al. |
| 9,433,780 B2 | 9/2016 | Regnier et al. |
| 9,457,193 B2 | 10/2016 | Klimovitch et al. |
| 9,492,668 B2 | 11/2016 | Sheldon et al. |
| 9,492,669 B2 | 11/2016 | Demmer et al. |
| 9,492,674 B2 | 11/2016 | Schmidt et al. |
| 9,492,677 B2 | 11/2016 | Greenhut et al. |
| 9,511,233 B2 | 12/2016 | Sambelashvili |
| 9,511,236 B2 | 12/2016 | Varady et al. |
| 9,511,237 B2 | 12/2016 | Deterre et al. |
| 9,522,276 B2 | 12/2016 | Shen et al. |
| 9,522,280 B2 | 12/2016 | Fishler et al. |
| 9,526,522 B2 | 12/2016 | Wood et al. |
| 9,526,891 B2 | 12/2016 | Eggen et al. |
| 9,526,909 B2 | 12/2016 | Stahmann et al. |
| 9,533,163 B2 | 1/2017 | Klimovitch et al. |
| 9,561,382 B2 | 2/2017 | Persson et al. |
| 9,566,012 B2 | 2/2017 | Greenhut et al. |
| 9,636,511 B2 | 5/2017 | Carney et al. |
| 9,669,223 B2 | 6/2017 | Auricchio et al. |
| 9,687,654 B2 | 6/2017 | Sheldon et al. |
| 9,687,655 B2 | 6/2017 | Pertijs et al. |
| 9,687,659 B2 | 6/2017 | Von Arx et al. |
| 9,694,186 B2 | 7/2017 | Carney et al. |
| 9,731,138 B1 | 8/2017 | Stadler et al. |
| 9,782,594 B2 | 10/2017 | Stahmann et al. |
| 9,782,601 B2 | 10/2017 | Ludwig |
| 9,789,317 B2 | 10/2017 | Greenhut et al. |
| 9,789,319 B2 | 10/2017 | Sambelashvili |
| 9,808,617 B2 | 11/2017 | Ostroff et al. |
| 9,808,628 B2 | 11/2017 | Sheldon et al. |
| 9,808,631 B2 | 11/2017 | Maile et al. |
| 9,808,632 B2 | 11/2017 | Reinke et al. |
| 9,808,633 B2 | 11/2017 | Bonner et al. |
| 9,808,637 B2 | 11/2017 | Sharma et al. |
| 9,855,414 B2 | 1/2018 | Marshall et al. |
| 9,855,430 B2 | 1/2018 | Ghosh et al. |
| 9,855,435 B2 | 1/2018 | Sahabi et al. |
| 9,861,815 B2 | 1/2018 | Tran et al. |
| 10,080,887 B2 | 9/2018 | Schmidt et al. |
| 10,080,888 B2 | 9/2018 | Kelly et al. |
| 10,080,900 B2 | 9/2018 | Ghosh et al. |
| 10,080,903 B2 | 9/2018 | Willis et al. |
| 10,086,206 B2 | 10/2018 | Sambelashvili |
| 10,118,026 B2 | 11/2018 | Grubac et al. |
| 10,124,163 B2 | 11/2018 | Ollivier et al. |
| 10,124,175 B2 | 11/2018 | Berthiaume et al. |
| 10,130,821 B2 | 11/2018 | Grubac et al. |
| 10,137,305 B2 | 11/2018 | Kane et al. |
| 10,201,710 B2 | 2/2019 | Jackson et al. |
| 10,207,115 B2 | 2/2019 | Echt et al. |
| 10,207,116 B2 | 2/2019 | Sheldon et al. |
| 10,226,197 B2 | 3/2019 | Reinke et al. |
| 10,226,639 B2 | 3/2019 | Zhang |
| 10,232,182 B2 | 3/2019 | Hareland et al. |
| 10,265,503 B2 | 4/2019 | Schmidt et al. |
| 10,265,534 B2 | 4/2019 | Greenhut et al. |
| 10,271,752 B2 | 4/2019 | Regnier et al. |
| 10,278,601 B2 | 5/2019 | Greenhut et al. |
| 10,279,165 B2 | 5/2019 | Seifert et al. |
| 10,286,221 B2 | 5/2019 | Sawchuk |
| 10,307,598 B2 | 6/2019 | Ciciarelli et al. |
| 10,328,274 B2 | 6/2019 | Zhang et al. |
| 10,342,981 B2 | 7/2019 | Ghosh et al. |
| 2002/0032470 A1 | 3/2002 | Linberg |
| 2002/0035376 A1 | 3/2002 | Bardy et al. |
| 2002/0035377 A1 | 3/2002 | Bardy et al. |
| 2002/0035378 A1 | 3/2002 | Bardy et al. |
| 2002/0035380 A1 | 3/2002 | Rissmann et al. |
| 2002/0035381 A1 | 3/2002 | Bardy et al. |
| 2002/0042629 A1 | 4/2002 | Bardy et al. |
| 2002/0042630 A1 | 4/2002 | Bardy et al. |
| 2002/0042634 A1 | 4/2002 | Bardy et al. |
| 2002/0049475 A1 | 4/2002 | Bardy et al. |
| 2002/0052636 A1 | 5/2002 | Bardy et al. |
| 2002/0068958 A1 | 6/2002 | Bardy et al. |
| 2002/0072773 A1 | 6/2002 | Bardy et al. |
| 2002/0082665 A1 | 6/2002 | Haller et al. |
| 2002/0091414 A1 | 7/2002 | Bardy et al. |
| 2002/0095196 A1 | 7/2002 | Linberg |
| 2002/0099423 A1 | 7/2002 | Berg et al. |
| 2002/0103510 A1 | 8/2002 | Bardy et al. |
| 2002/0107545 A1 | 8/2002 | Rissmann et al. |
| 2002/0107546 A1 | 8/2002 | Ostroff et al. |
| 2002/0107547 A1 | 8/2002 | Edinger et al. |
| 2002/0107548 A1 | 8/2002 | Bardy et al. |
| 2002/0107549 A1 | 8/2002 | Bardy et al. |
| 2002/0107559 A1 | 8/2002 | Sanders et al. |
| 2002/0120299 A1 | 8/2002 | Ostroff et al. |
| 2002/0173830 A1 | 11/2002 | Starkweather et al. |
| 2002/0193846 A1 | 12/2002 | Pool et al. |
| 2003/0009203 A1 | 1/2003 | Lebel et al. |
| 2003/0028082 A1 | 2/2003 | Thompson |
| 2003/0040779 A1 | 2/2003 | Engmark et al. |
| 2003/0041866 A1 | 3/2003 | Linberg et al. |
| 2003/0045805 A1 | 3/2003 | Sheldon et al. |
| 2003/0088278 A1 | 5/2003 | Bardy et al. |
| 2003/0097153 A1 | 5/2003 | Bardy et al. |

(56) References Cited

U.S. PATENT DOCUMENTS

| | | |
|---|---|---|
| 2003/0105497 A1 | 6/2003 | Zhu et al. |
| 2003/0114908 A1 | 6/2003 | Flach |
| 2003/0144701 A1 | 7/2003 | Mehra et al. |
| 2003/0187460 A1 | 10/2003 | Chin et al. |
| 2003/0187461 A1 | 10/2003 | Chin |
| 2004/0024435 A1 | 2/2004 | Leckrone et al. |
| 2004/0068302 A1 | 4/2004 | Rodgers et al. |
| 2004/0087938 A1 | 5/2004 | Leckrone et al. |
| 2004/0088035 A1 | 5/2004 | Guenst et al. |
| 2004/0102830 A1 | 5/2004 | Williams |
| 2004/0127959 A1 | 7/2004 | Amundson et al. |
| 2004/0133242 A1 | 7/2004 | Chapman et al. |
| 2004/0147969 A1 | 7/2004 | Mann et al. |
| 2004/0147973 A1 | 7/2004 | Hauser |
| 2004/0167558 A1 | 8/2004 | Igo et al. |
| 2004/0167587 A1 | 8/2004 | Thompson |
| 2004/0172071 A1 | 9/2004 | Bardy et al. |
| 2004/0172077 A1 | 9/2004 | Chinchoy |
| 2004/0172104 A1 | 9/2004 | Berg et al. |
| 2004/0176817 A1 | 9/2004 | Wahlstrand et al. |
| 2004/0176818 A1 | 9/2004 | Wahlstrand et al. |
| 2004/0176830 A1 | 9/2004 | Fang |
| 2004/0186529 A1 | 9/2004 | Bardy et al. |
| 2004/0204673 A1 | 10/2004 | Flaherty |
| 2004/0210292 A1 | 10/2004 | Bardy et al. |
| 2004/0210293 A1 | 10/2004 | Bardy et al. |
| 2004/0210294 A1 | 10/2004 | Bardy et al. |
| 2004/0215308 A1 | 10/2004 | Bardy et al. |
| 2004/0220624 A1 | 11/2004 | Ritscher et al. |
| 2004/0220626 A1 | 11/2004 | Wagner |
| 2004/0220639 A1 | 11/2004 | Mulligan et al. |
| 2004/0230283 A1 | 11/2004 | Prinzen et al. |
| 2004/0249431 A1 | 12/2004 | Ransbury et al. |
| 2004/0260348 A1 | 12/2004 | Bakken et al. |
| 2004/0267303 A1 | 12/2004 | Guenst |
| 2005/0061320 A1 | 3/2005 | Lee et al. |
| 2005/0070962 A1 | 3/2005 | Echt et al. |
| 2005/0102003 A1 | 5/2005 | Grabek et al. |
| 2005/0149138 A1 | 7/2005 | Min et al. |
| 2005/0165466 A1 | 7/2005 | Morris et al. |
| 2005/0182465 A1 | 8/2005 | Ness |
| 2005/0203410 A1 | 9/2005 | Jenkins |
| 2005/0283208 A1 | 12/2005 | Von Arx et al. |
| 2005/0288743 A1 | 12/2005 | Ahn et al. |
| 2006/0042830 A1 | 3/2006 | Maghribi et al. |
| 2006/0052829 A1 | 3/2006 | Sun et al. |
| 2006/0052830 A1 | 3/2006 | Spinelli et al. |
| 2006/0064135 A1 | 3/2006 | Brockway |
| 2006/0064149 A1 | 3/2006 | Belacazar et al. |
| 2006/0085039 A1 | 4/2006 | Hastings et al. |
| 2006/0085041 A1 | 4/2006 | Hastings et al. |
| 2006/0085042 A1 | 4/2006 | Hastings et al. |
| 2006/0095078 A1 | 5/2006 | Tronnes |
| 2006/0106442 A1 | 5/2006 | Richardson et al. |
| 2006/0116746 A1 | 6/2006 | Chin |
| 2006/0135999 A1 | 6/2006 | Bodner et al. |
| 2006/0136004 A1 | 6/2006 | Cowan et al. |
| 2006/0161061 A1 | 7/2006 | Echt et al. |
| 2006/0200002 A1 | 9/2006 | Guenst |
| 2006/0206151 A1 | 9/2006 | Lu |
| 2006/0212079 A1 | 9/2006 | Routh et al. |
| 2006/0241701 A1 | 10/2006 | Markowitz et al. |
| 2006/0241705 A1 | 10/2006 | Neumann et al. |
| 2006/0247672 A1 | 11/2006 | Vidlund et al. |
| 2006/0259088 A1 | 11/2006 | Pastore et al. |
| 2006/0265018 A1 | 11/2006 | Smith et al. |
| 2007/0004979 A1 | 1/2007 | Wojciechowicz et al. |
| 2007/0016098 A1 | 1/2007 | Kim et al. |
| 2007/0027508 A1 | 2/2007 | Cowan |
| 2007/0078490 A1 | 4/2007 | Cowan et al. |
| 2007/0088394 A1 | 4/2007 | Jacobson |
| 2007/0088396 A1 | 4/2007 | Jacobson |
| 2007/0088397 A1 | 4/2007 | Jacobson |
| 2007/0088398 A1 | 4/2007 | Jacobson |
| 2007/0088405 A1 | 4/2007 | Jacobson |
| 2007/0135882 A1 | 6/2007 | Drasler et al. |
| 2007/0135883 A1 | 6/2007 | Drasler et al. |
| 2007/0150037 A1 | 6/2007 | Hastings et al. |
| 2007/0150038 A1 | 6/2007 | Hastings et al. |
| 2007/0156190 A1 | 7/2007 | Cinbis |
| 2007/0219525 A1 | 9/2007 | Gelfand et al. |
| 2007/0219590 A1 | 9/2007 | Hastings et al. |
| 2007/0225545 A1 | 9/2007 | Ferrari |
| 2007/0233206 A1 | 10/2007 | Frikart et al. |
| 2007/0239244 A1 | 10/2007 | Morgan et al. |
| 2007/0255376 A1 | 11/2007 | Michels et al. |
| 2007/0276444 A1 | 11/2007 | Gelbart et al. |
| 2007/0293900 A1 | 12/2007 | Sheldon et al. |
| 2007/0293904 A1 | 12/2007 | Gelbart et al. |
| 2008/0004663 A1 | 1/2008 | Jorgenson |
| 2008/0021505 A1 | 1/2008 | Hastings et al. |
| 2008/0021519 A1 | 1/2008 | De Geest et al. |
| 2008/0021532 A1 | 1/2008 | Kveen et al. |
| 2008/0065183 A1 | 3/2008 | Whitehurst et al. |
| 2008/0065185 A1 | 3/2008 | Worley |
| 2008/0071318 A1 | 3/2008 | Brooke et al. |
| 2008/0109054 A1 | 5/2008 | Hastings et al. |
| 2008/0119911 A1 | 5/2008 | Rosero |
| 2008/0130670 A1 | 6/2008 | Kim et al. |
| 2008/0154139 A1 | 6/2008 | Shuros et al. |
| 2008/0154322 A1 | 6/2008 | Jackson et al. |
| 2008/0228234 A1 | 9/2008 | Stancer |
| 2008/0234771 A1 | 9/2008 | Chinchoy et al. |
| 2008/0243217 A1 | 10/2008 | Wildon |
| 2008/0269814 A1 | 10/2008 | Rosero |
| 2008/0269825 A1 | 10/2008 | Chinchoy et al. |
| 2008/0275518 A1 | 11/2008 | Ghanem et al. |
| 2008/0275519 A1 | 11/2008 | Ghanem et al. |
| 2008/0288039 A1 | 11/2008 | Reddy |
| 2008/0294208 A1 | 11/2008 | Willis et al. |
| 2008/0294210 A1 | 11/2008 | Rosero |
| 2008/0294229 A1 | 11/2008 | Friedman et al. |
| 2008/0306359 A1 | 12/2008 | Zdeblick et al. |
| 2009/0018599 A1 | 1/2009 | Hastings et al. |
| 2009/0024180 A1 | 1/2009 | Kisker et al. |
| 2009/0036941 A1 | 2/2009 | Corbucci |
| 2009/0048646 A1 | 2/2009 | Katoozi et al. |
| 2009/0062895 A1 | 3/2009 | Stahmann et al. |
| 2009/0082827 A1 | 3/2009 | Kveen et al. |
| 2009/0082828 A1 | 3/2009 | Ostroff |
| 2009/0088813 A1 | 4/2009 | Brockway et al. |
| 2009/0131907 A1 | 5/2009 | Chin et al. |
| 2009/0135886 A1 | 5/2009 | Robertson et al. |
| 2009/0143835 A1 | 6/2009 | Pastore et al. |
| 2009/0171408 A1 | 7/2009 | Solem |
| 2009/0171414 A1 | 7/2009 | Kelly et al. |
| 2009/0204163 A1 | 8/2009 | Shuros et al. |
| 2009/0204170 A1* | 8/2009 | Hastings .............. A61N 1/3756 607/33 |
| 2009/0210024 A1 | 8/2009 | M. |
| 2009/0216292 A1 | 8/2009 | Pless et al. |
| 2009/0234407 A1 | 9/2009 | Hastings et al. |
| 2009/0234411 A1 | 9/2009 | Sambelashvili et al. |
| 2009/0266573 A1 | 10/2009 | Engmark et al. |
| 2009/0275998 A1 | 11/2009 | Burnes et al. |
| 2009/0275999 A1 | 11/2009 | Burnes et al. |
| 2009/0299447 A1 | 12/2009 | Jensen et al. |
| 2010/0013668 A1 | 1/2010 | Kantervik |
| 2010/0016911 A1 | 1/2010 | Willis et al. |
| 2010/0023085 A1 | 1/2010 | Wu et al. |
| 2010/0030061 A1 | 2/2010 | Canfield et al. |
| 2010/0030327 A1 | 2/2010 | Chatel |
| 2010/0042108 A1 | 2/2010 | Hibino |
| 2010/0056871 A1 | 3/2010 | Govari et al. |
| 2010/0063375 A1 | 3/2010 | Kassab et al. |
| 2010/0063562 A1 | 3/2010 | Cowan et al. |
| 2010/0069983 A1 | 3/2010 | Peacock, III et al. |
| 2010/0094367 A1 | 4/2010 | Sen |
| 2010/0114209 A1 | 5/2010 | Krause et al. |
| 2010/0114214 A1 | 5/2010 | Morelli et al. |
| 2010/0125281 A1 | 5/2010 | Jacobson et al. |
| 2010/0168761 A1 | 7/2010 | Kassab et al. |
| 2010/0168819 A1 | 7/2010 | Freeberg |
| 2010/0198288 A1 | 8/2010 | Ostroff |

(56) References Cited

U.S. PATENT DOCUMENTS

| | | |
|---|---|---|
| 2010/0198304 A1 | 8/2010 | Wang |
| 2010/0217367 A1 | 8/2010 | Belson |
| 2010/0228308 A1 | 9/2010 | Cowan et al. |
| 2010/0234906 A1 | 9/2010 | Koh |
| 2010/0234924 A1 | 9/2010 | Willis |
| 2010/0241185 A1 | 9/2010 | Mahapatra et al. |
| 2010/0249729 A1 | 9/2010 | Morris et al. |
| 2010/0286744 A1 | 11/2010 | Echt et al. |
| 2010/0298841 A1 | 11/2010 | Prinzen et al. |
| 2010/0312309 A1 | 12/2010 | Harding |
| 2011/0022113 A1 | 1/2011 | Zdeblick et al. |
| 2011/0071586 A1 | 3/2011 | Jacobson |
| 2011/0077708 A1 | 3/2011 | Ostroff |
| 2011/0112600 A1 | 5/2011 | Cowan et al. |
| 2011/0118588 A1 | 5/2011 | Komblau et al. |
| 2011/0118810 A1 | 5/2011 | Cowan et al. |
| 2011/0137187 A1 | 6/2011 | Fang et al. |
| 2011/0144720 A1 | 6/2011 | Cowan et al. |
| 2011/0152970 A1 | 6/2011 | Jollota et al. |
| 2011/0160558 A1 | 6/2011 | Rassatt et al. |
| 2011/0160565 A1 | 6/2011 | Stubbs et al. |
| 2011/0160801 A1 | 6/2011 | Markowitz et al. |
| 2011/0160806 A1 | 6/2011 | Lyden et al. |
| 2011/0166620 A1 | 7/2011 | Cowan et al. |
| 2011/0166621 A1 | 7/2011 | Cowan et al. |
| 2011/0184491 A1 | 7/2011 | Kivi |
| 2011/0190835 A1 | 8/2011 | Brockway et al. |
| 2011/0208260 A1 | 8/2011 | Jacobson |
| 2011/0218587 A1 | 9/2011 | Jacobson |
| 2011/0230734 A1 | 9/2011 | Fain et al. |
| 2011/0237967 A1 | 9/2011 | Moore et al. |
| 2011/0245890 A1 | 10/2011 | Brisben et al. |
| 2011/0251660 A1 | 10/2011 | Griswold |
| 2011/0251662 A1 | 10/2011 | Griswold et al. |
| 2011/0270099 A1 | 11/2011 | Ruben et al. |
| 2011/0270339 A1 | 11/2011 | Murray, III et al. |
| 2011/0270340 A1 | 11/2011 | Pellegrini et al. |
| 2011/0270341 A1 | 11/2011 | Ruben et al. |
| 2011/0276102 A1 | 11/2011 | Cohen |
| 2011/0282423 A1 | 11/2011 | Jacobson |
| 2012/0004527 A1 | 1/2012 | Thompson et al. |
| 2012/0029323 A1 | 2/2012 | Zhao |
| 2012/0041508 A1 | 2/2012 | Rousso et al. |
| 2012/0059433 A1 | 3/2012 | Cowan et al. |
| 2012/0059436 A1 | 3/2012 | Fontaine et al. |
| 2012/0065500 A1 | 3/2012 | Rogers et al. |
| 2012/0078322 A1 | 3/2012 | Molin et al. |
| 2012/0089198 A1 | 4/2012 | Ostroff |
| 2012/0093245 A1 | 4/2012 | Makdissi et al. |
| 2012/0095521 A1 | 4/2012 | Hintz |
| 2012/0095539 A1 | 4/2012 | Khairkhahan et al. |
| 2012/0101540 A1 | 4/2012 | O'Brien et al. |
| 2012/0101553 A1 | 4/2012 | Reddy |
| 2012/0109148 A1 | 5/2012 | Bonner et al. |
| 2012/0109149 A1 | 5/2012 | Bonner et al. |
| 2012/0109236 A1 | 5/2012 | Jacobson et al. |
| 2012/0109259 A1 | 5/2012 | Bond et al. |
| 2012/0116489 A1 | 5/2012 | Khairkhahan et al. |
| 2012/0150251 A1 | 6/2012 | Giftakis et al. |
| 2012/0158111 A1 | 6/2012 | Khairkhahan et al. |
| 2012/0165827 A1 | 6/2012 | Khairkhahan et al. |
| 2012/0172690 A1 | 7/2012 | Anderson et al. |
| 2012/0172891 A1 | 7/2012 | Lee |
| 2012/0172892 A1 | 7/2012 | Grubac et al. |
| 2012/0172942 A1 | 7/2012 | Berg |
| 2012/0197350 A1 | 8/2012 | Roberts et al. |
| 2012/0197373 A1 | 8/2012 | Khairkhahan et al. |
| 2012/0215285 A1 | 8/2012 | Tahmasian et al. |
| 2012/0232565 A1 | 9/2012 | Kveen et al. |
| 2012/0245665 A1 | 9/2012 | Friedman et al. |
| 2012/0277600 A1 | 11/2012 | Greenhut |
| 2012/0277606 A1 | 11/2012 | Ellingson et al. |
| 2012/0283795 A1 | 11/2012 | Stancer et al. |
| 2012/0283807 A1 | 11/2012 | Deterre et al. |
| 2012/0289776 A1 | 11/2012 | Keast et al. |
| 2012/0289815 A1 | 11/2012 | Keast et al. |
| 2012/0290021 A1 | 11/2012 | Saurkar et al. |
| 2012/0290025 A1 | 11/2012 | Keimel |
| 2012/0296381 A1 | 11/2012 | Matos |
| 2012/0303082 A1 | 11/2012 | Dong et al. |
| 2012/0316613 A1 | 12/2012 | Keefe et al. |
| 2013/0012151 A1 | 1/2013 | Hankins |
| 2013/0023975 A1 | 1/2013 | Locsin |
| 2013/0035748 A1 | 2/2013 | Bonner et al. |
| 2013/0041422 A1 | 2/2013 | Jacobson |
| 2013/0053908 A1 | 2/2013 | Smith et al. |
| 2013/0053915 A1 | 2/2013 | Holmstrom et al. |
| 2013/0053921 A1 | 2/2013 | Bonner et al. |
| 2013/0060298 A1 | 3/2013 | Splett et al. |
| 2013/0066169 A1 | 3/2013 | Rys et al. |
| 2013/0072770 A1 | 3/2013 | Rao et al. |
| 2013/0079798 A1 | 3/2013 | Tran et al. |
| 2013/0079861 A1 | 3/2013 | Reinert et al. |
| 2013/0085350 A1 | 4/2013 | Schugt et al. |
| 2013/0085403 A1 | 4/2013 | Gunderson et al. |
| 2013/0085550 A1 | 4/2013 | Polefko et al. |
| 2013/0096649 A1 | 4/2013 | Martin et al. |
| 2013/0103047 A1 | 4/2013 | Steingisser et al. |
| 2013/0103109 A1 | 4/2013 | Jacobson |
| 2013/0110008 A1 | 5/2013 | Bourget et al. |
| 2013/0110127 A1 | 5/2013 | Bornzin et al. |
| 2013/0110192 A1 | 5/2013 | Tran et al. |
| 2013/0110219 A1 | 5/2013 | Bornzin et al. |
| 2013/0116529 A1 | 5/2013 | Min et al. |
| 2013/0116738 A1 | 5/2013 | Samade et al. |
| 2013/0116740 A1* | 5/2013 | Bornzin ............... A61N 1/3756 607/9 |
| 2013/0116741 A1 | 5/2013 | Bornzin et al. |
| 2013/0123872 A1 | 5/2013 | Bornzin et al. |
| 2013/0123875 A1 | 5/2013 | Varady et al. |
| 2013/0131591 A1 | 5/2013 | Berthiaume et al. |
| 2013/0131693 A1 | 5/2013 | Berthiaume et al. |
| 2013/0138006 A1 | 5/2013 | Bornzin et al. |
| 2013/0150695 A1 | 6/2013 | Biela et al. |
| 2013/0150911 A1 | 6/2013 | Perschbacher et al. |
| 2013/0150912 A1 | 6/2013 | Perschbacher et al. |
| 2013/0184776 A1 | 7/2013 | Shuros et al. |
| 2013/0192611 A1 | 8/2013 | Taepke, II et al. |
| 2013/0196703 A1 | 8/2013 | Masoud et al. |
| 2013/0197609 A1 | 8/2013 | Moore et al. |
| 2013/0231710 A1 | 9/2013 | Jacobson |
| 2013/0238072 A1 | 9/2013 | Deterre et al. |
| 2013/0238073 A1 | 9/2013 | Makdissi et al. |
| 2013/0253309 A1 | 9/2013 | Allan et al. |
| 2013/0253342 A1 | 9/2013 | Griswold et al. |
| 2013/0253343 A1 | 9/2013 | Waldhauser et al. |
| 2013/0253344 A1 | 9/2013 | Griswold et al. |
| 2013/0253345 A1 | 9/2013 | Griswold et al. |
| 2013/0253346 A1 | 9/2013 | Griswold et al. |
| 2013/0253347 A1 | 9/2013 | Griswold et al. |
| 2013/0261497 A1 | 10/2013 | Pertijs et al. |
| 2013/0265144 A1 | 10/2013 | Banna et al. |
| 2013/0268042 A1 | 10/2013 | Hastings et al. |
| 2013/0274828 A1 | 10/2013 | Willis |
| 2013/0274847 A1 | 10/2013 | Ostroff |
| 2013/0282070 A1 | 10/2013 | Cowan et al. |
| 2013/0282073 A1 | 10/2013 | Cowan et al. |
| 2013/0296727 A1 | 11/2013 | Sullivan et al. |
| 2013/0303872 A1 | 11/2013 | Taff et al. |
| 2013/0324825 A1 | 12/2013 | Ostroff et al. |
| 2013/0325081 A1 | 12/2013 | Karst et al. |
| 2013/0345770 A1 | 12/2013 | Dianaty et al. |
| 2014/0012344 A1 | 1/2014 | Hastings et al. |
| 2014/0018876 A1 | 1/2014 | Ostroff |
| 2014/0018877 A1 | 1/2014 | Demmer et al. |
| 2014/0031836 A1 | 1/2014 | Ollivier |
| 2014/0039570 A1 | 2/2014 | Carroll et al. |
| 2014/0039591 A1 | 2/2014 | Drasler et al. |
| 2014/0043146 A1 | 2/2014 | Makdissi et al. |
| 2014/0046395 A1 | 2/2014 | Regnier et al. |
| 2014/0046420 A1 | 2/2014 | Moore et al. |
| 2014/0058240 A1 | 2/2014 | Mothilal et al. |
| 2014/0058494 A1 | 2/2014 | Ostroff et al. |
| 2014/0074114 A1 | 3/2014 | Khairkhahan et al. |

(56) References Cited

U.S. PATENT DOCUMENTS

| | | |
|---|---|---|
| 2014/0074186 A1 | 3/2014 | Faltys et al. |
| 2014/0094891 A1 | 4/2014 | Pare et al. |
| 2014/0100624 A1 | 4/2014 | Ellingson |
| 2014/0100627 A1 | 4/2014 | Min |
| 2014/0107723 A1 | 4/2014 | Hou et al. |
| 2014/0121719 A1 | 5/2014 | Bonner et al. |
| 2014/0121720 A1 | 5/2014 | Bonner et al. |
| 2014/0121722 A1 | 5/2014 | Sheldon et al. |
| 2014/0128935 A1 | 5/2014 | Kumar et al. |
| 2014/0135865 A1 | 5/2014 | Hastings et al. |
| 2014/0142648 A1 | 5/2014 | Smith et al. |
| 2014/0148675 A1 | 5/2014 | Nordstrom et al. |
| 2014/0148815 A1 | 5/2014 | Wenzel et al. |
| 2014/0155950 A1 | 6/2014 | Hastings et al. |
| 2014/0169162 A1 | 6/2014 | Romano et al. |
| 2014/0172060 A1 | 6/2014 | Bornzin et al. |
| 2014/0180306 A1 | 6/2014 | Grubac et al. |
| 2014/0180366 A1 | 6/2014 | Edlund |
| 2014/0207149 A1 | 7/2014 | Hastings et al. |
| 2014/0207210 A1 | 7/2014 | Willis et al. |
| 2014/0214104 A1 | 7/2014 | Greenhut et al. |
| 2014/0222015 A1 | 8/2014 | Keast et al. |
| 2014/0222098 A1 | 8/2014 | Baru et al. |
| 2014/0222109 A1 | 8/2014 | Moulder |
| 2014/0228913 A1 | 8/2014 | Molin et al. |
| 2014/0236172 A1 | 8/2014 | Hastings et al. |
| 2014/0243848 A1 | 8/2014 | Auricchio et al. |
| 2014/0255298 A1 | 9/2014 | Cole et al. |
| 2014/0257324 A1 | 9/2014 | Fain |
| 2014/0257422 A1 | 9/2014 | Herken |
| 2014/0257444 A1 | 9/2014 | Cole et al. |
| 2014/0276929 A1 | 9/2014 | Foster et al. |
| 2014/0303704 A1 | 10/2014 | Suwito et al. |
| 2014/0309706 A1 | 10/2014 | Jacobson |
| 2014/0343348 A1 | 11/2014 | Kaplan et al. |
| 2014/0371818 A1 | 12/2014 | Bond et al. |
| 2014/0379041 A1 | 12/2014 | Foster |
| 2015/0025612 A1 | 1/2015 | Haasl et al. |
| 2015/0039041 A1 | 2/2015 | Smith et al. |
| 2015/0045868 A1 | 2/2015 | Bonner et al. |
| 2015/0051609 A1 | 2/2015 | Schmidt et al. |
| 2015/0051610 A1 | 2/2015 | Schmidt et al. |
| 2015/0051611 A1 | 2/2015 | Schmidt et al. |
| 2015/0051612 A1 | 2/2015 | Schmidt et al. |
| 2015/0051613 A1 | 2/2015 | Schmidt et al. |
| 2015/0051614 A1 | 2/2015 | Schmidt et al. |
| 2015/0051615 A1 | 2/2015 | Schmidt et al. |
| 2015/0051616 A1 | 2/2015 | Haasl et al. |
| 2015/0051682 A1 | 2/2015 | Schmidt et al. |
| 2015/0057520 A1 | 2/2015 | Foster et al. |
| 2015/0057558 A1 | 2/2015 | Stahmann et al. |
| 2015/0057721 A1 | 2/2015 | Stahmann et al. |
| 2015/0088155 A1 | 3/2015 | Stahmann et al. |
| 2015/0105836 A1 | 4/2015 | Bonner et al. |
| 2015/0126854 A1 | 5/2015 | Keast et al. |
| 2015/0157861 A1 | 6/2015 | Aghassian |
| 2015/0157866 A1 | 6/2015 | Demmer et al. |
| 2015/0173655 A1 | 6/2015 | Demmer et al. |
| 2015/0190638 A1 | 7/2015 | Smith et al. |
| 2015/0196756 A1 | 7/2015 | Stahmann et al. |
| 2015/0196757 A1 | 7/2015 | Stahmann et al. |
| 2015/0196758 A1 | 7/2015 | Stahmann et al. |
| 2015/0196769 A1 | 7/2015 | Stahmann et al. |
| 2015/0217119 A1 | 8/2015 | Nikolski et al. |
| 2015/0221898 A1 | 8/2015 | Chi et al. |
| 2015/0224315 A1 | 8/2015 | Stahmann |
| 2015/0224320 A1 | 8/2015 | Stahmann |
| 2015/0230699 A1 | 8/2015 | Berul et al. |
| 2015/0238769 A1 | 8/2015 | Demmer et al. |
| 2015/0258345 A1 | 9/2015 | Smith et al. |
| 2015/0290468 A1 | 10/2015 | Zhang |
| 2015/0297905 A1 | 10/2015 | Greenhut et al. |
| 2015/0297907 A1 | 10/2015 | Zhang |
| 2015/0305637 A1 | 10/2015 | Greenhut et al. |
| 2015/0305638 A1 | 10/2015 | Zhang |
| 2015/0305639 A1 | 10/2015 | Greenhut et al. |
| 2015/0305640 A1 | 10/2015 | Reinke et al. |
| 2015/0305641 A1 | 10/2015 | Stadler et al. |
| 2015/0305642 A1 | 10/2015 | Reinke et al. |
| 2015/0306374 A1 | 10/2015 | Seifert et al. |
| 2015/0306375 A1 | 10/2015 | Marshall et al. |
| 2015/0306401 A1 | 10/2015 | Demmer et al. |
| 2015/0306406 A1 | 10/2015 | Crutchfield et al. |
| 2015/0306407 A1 | 10/2015 | Crutchfield et al. |
| 2015/0306408 A1 | 10/2015 | Greenhut et al. |
| 2015/0321016 A1 | 11/2015 | O'Brien et al. |
| 2015/0328459 A1 | 11/2015 | Chin et al. |
| 2015/0335884 A1 | 11/2015 | Khairkhahan et al. |
| 2016/0015322 A1 | 1/2016 | Anderson et al. |
| 2016/0023000 A1 | 1/2016 | Cho et al. |
| 2016/0030757 A1 | 2/2016 | Jacobson |
| 2016/0033177 A1 | 2/2016 | Barot et al. |
| 2016/0121127 A1 | 5/2016 | Klimovitch et al. |
| 2016/0121128 A1 | 5/2016 | Fishler et al. |
| 2016/0121129 A1 | 5/2016 | Persson et al. |
| 2016/0136440 A1 | 5/2016 | Min et al. |
| 2016/0213919 A1 | 7/2016 | Suwito et al. |
| 2016/0213937 A1 | 7/2016 | Reinke et al. |
| 2016/0213939 A1 | 7/2016 | Carney et al. |
| 2016/0228026 A1 | 8/2016 | Jackson |
| 2016/0317825 A1 | 11/2016 | Jacobson |
| 2016/0367823 A1 | 12/2016 | Cowan et al. |
| 2017/0014629 A1 | 1/2017 | Ghosh et al. |
| 2017/0035315 A1 | 2/2017 | Jackson |
| 2017/0043173 A1 | 2/2017 | Sharma et al. |
| 2017/0043174 A1 | 2/2017 | Greenhut et al. |
| 2017/0182327 A1 | 6/2017 | Liu |
| 2017/0189681 A1 | 7/2017 | Anderson |
| 2017/0281261 A1 | 10/2017 | Shuros et al. |
| 2017/0281952 A1 | 10/2017 | Shuros et al. |
| 2017/0281953 A1 | 10/2017 | Min et al. |
| 2017/0281955 A1 | 10/2017 | Maile et al. |
| 2017/0312531 A1 | 11/2017 | Sawchuk |
| 2018/0256902 A1 | 9/2018 | Toy et al. |
| 2018/0256909 A1 | 9/2018 | Smith et al. |
| 2018/0264262 A1 | 9/2018 | Haasl et al. |
| 2018/0264270 A1 | 9/2018 | Koop et al. |
| 2018/0264272 A1 | 9/2018 | Haasl et al. |
| 2018/0264273 A1 | 9/2018 | Haasl et al. |
| 2018/0264274 A1 | 9/2018 | Haasl et al. |
| 2018/0339160 A1 | 11/2018 | Carroll |
| 2019/0083801 A1* | 3/2019 | Yang ................. A61N 1/37518 |
| 2020/0101300 A1* | 4/2020 | Li ....................... A61N 1/37229 |

FOREIGN PATENT DOCUMENTS

| | | | |
|---|---|---|---|
| AU | 2014203793 | A1 | 7/2014 |
| CA | 1003904 | A1 | 1/1977 |
| CN | 202933393 | U | 5/2013 |
| EP | 0362611 | A1 | 4/1990 |
| EP | 503823 | A2 | 9/1992 |
| EP | 1702648 | A2 | 9/2006 |
| EP | 1904166 | B1 | 6/2011 |
| EP | 2471452 | A1 | 7/2012 |
| EP | 2433675 | B1 | 1/2013 |
| EP | 2441491 | B1 | 1/2013 |
| EP | 2452721 | B1 | 11/2013 |
| EP | 2662113 | A3 | 11/2013 |
| EP | 1948296 | B1 | 1/2014 |
| EP | 2760541 | B1 | 5/2016 |
| EP | 2833966 | B1 | 5/2016 |
| JP | 2000051373 | A | 2/2000 |
| JP | 2002502640 | A | 1/2002 |
| JP | 2004512105 | A | 4/2004 |
| JP | 2005508208 | A | 3/2005 |
| JP | 2005245215 | A | 9/2005 |
| JP | 2008540040 | A | 11/2008 |
| JP | 5199867 | B2 | 2/2013 |
| WO | 9500202 | A1 | 1/1995 |
| WO | 9636134 | A1 | 11/1996 |
| WO | 9724981 | A2 | 7/1997 |
| WO | 9826840 | A1 | 6/1998 |
| WO | 9939767 | A1 | 8/1999 |
| WO | 0234330 | A2 | 5/2002 |

(56) References Cited

FOREIGN PATENT DOCUMENTS

| WO | 02098282 A2 | 12/2002 |
| WO | 2005000206 A3 | 1/2005 |
| WO | 2005042089 A1 | 5/2005 |
| WO | 2006065394 A1 | 6/2006 |
| WO | 2006086435 A3 | 8/2006 |
| WO | 2006113659 A1 | 10/2006 |
| WO | 2006124833 A2 | 11/2006 |
| WO | 2006124833 A3 | 11/2006 |
| WO | 2007073435 A1 | 6/2007 |
| WO | 2007075974 A2 | 7/2007 |
| WO | 2009006531 A1 | 1/2009 |
| WO | 2012054102 A1 | 4/2012 |
| WO | 2013080038 A2 | 6/2013 |
| WO | 2013098644 A3 | 7/2013 |
| WO | 2013184787 A1 | 12/2013 |
| WO | 2014120769 A1 | 8/2014 |

OTHER PUBLICATIONS

"Instructions for Use System 1, Leadless Cardiac Pacemaker (LCP) and Delivery Catheter," Nanostim Leadless Pacemakers, pp. 1-28, 2013.

Hachisuka et al., "Development and Performance Analysis of an Intra-Body Communication Device," The 12th International Conference on Solid State Sensors, Actuators and Microsystems, vol. 4A1.3, pp. 1722-1725, 2003.

Seyedi et al., "A Survey on Intrabody Communications for Body Area Network Application," IEEE Transactions on Biomedical Engineering, vol. 60(8): 2067-2079, 2013.

Spickler et al., "Totally Self-Contained Intracardiac Pacemaker," Journal of Electrocardiology, vol. 3(384): 324-331, 1970.

Wegmüller, "Intra-Body Communication for Biomedical Sensor Networks," Diss. EIH, No. 17323, 1-173, 2007.

\* cited by examiner

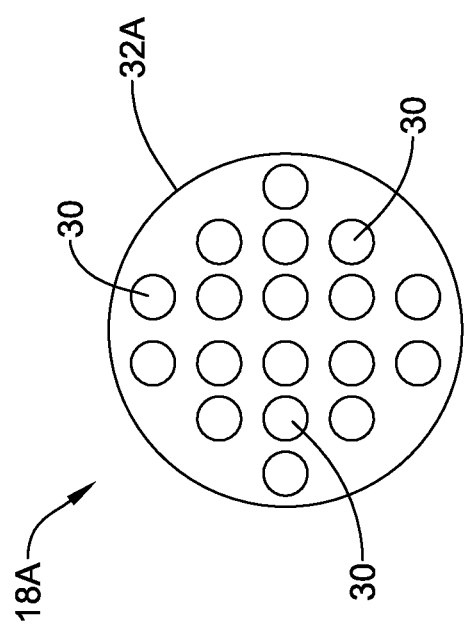

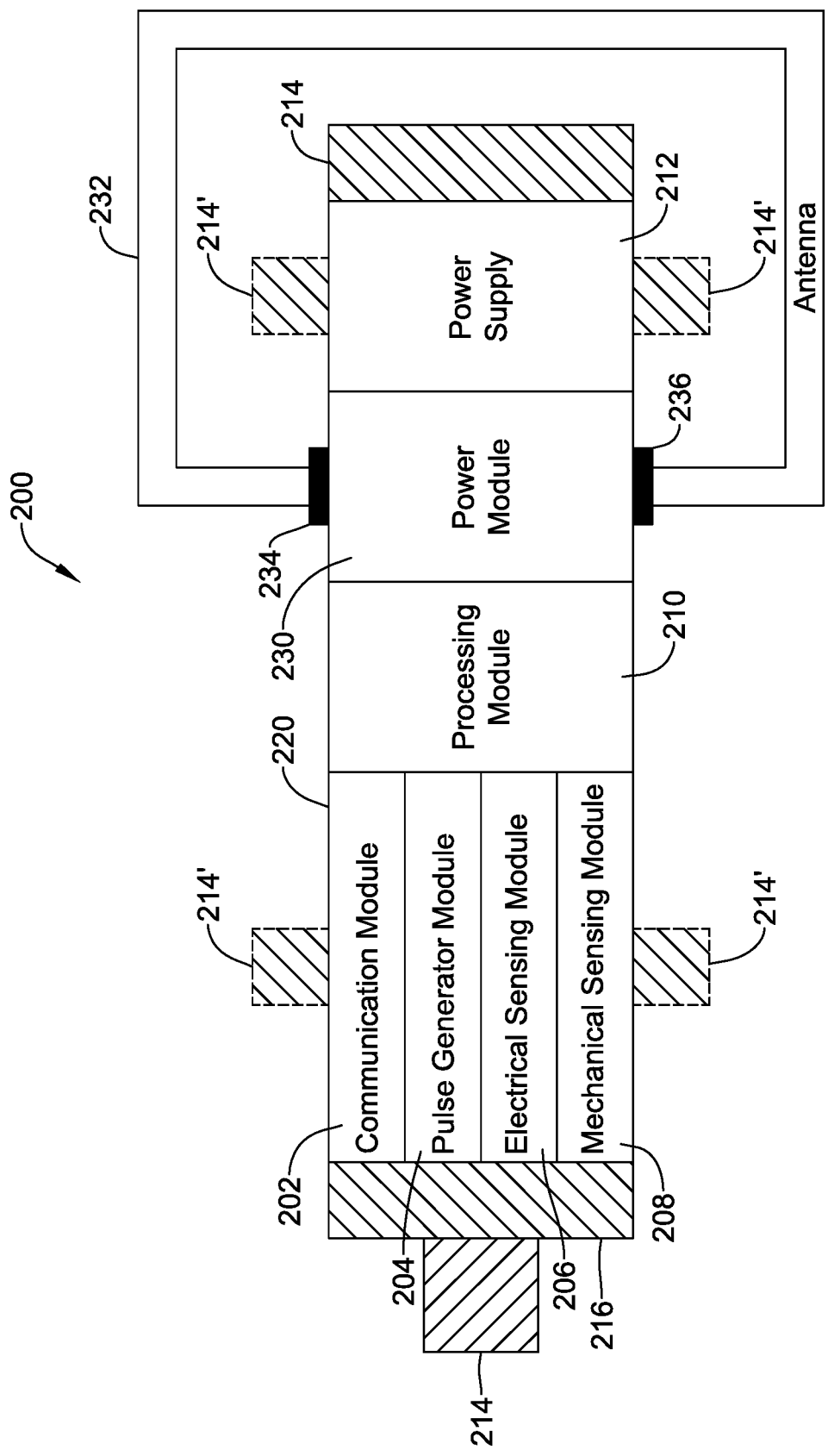

LEADLESS CARDIAC PACEMAKER FOR BUNDLE OF HIS PACING

CROSS REFERENCE TO RELATED APPLICATIONS

This application claims the benefit of U.S. Provisional Patent Application Ser. No. 62/582,724 filed on Nov. 7, 2017, the disclosure of which is incorporated herein by reference.

TECHNICAL FIELD

The present disclosure pertains to medical devices, and more particularly to implantable medical devices such as leadless cardiac pacemakers.

BACKGROUND

Implantable medical devices are commonly used today to monitor physiological or other parameters of a patient and/or deliver therapy to a patient. In one example, to help patients with heart related conditions, various medical devices (e.g., pacemakers, defibrillators, etc.) can be implanted in a patient's body. Such devices may monitor and in some cases provide electrical stimulation (e.g. pacing, defibrillation, etc.) to the heart to help the heart operate in a more normal, efficient and/or safe manner.

SUMMARY

The present disclosure pertains to medical devices, and more particularly to leadless cardiac pacemakers that are configured for atrial placement. In some cases, a leadless cardiac pacemaker may be configured to be anchored within the right atrium. In some cases, a leadless cardiac pacemaker may be configured to pace the ventricles by pacing the bundle of His.

In one example, a leadless cardiac pacemaker (LCP) is configured for atrial placement. The LCP includes a housing, two or more electrodes and a controller that is disposed within the housing and is operably coupled to the two or more electrodes. The controller is configured to deliver pacing therapy via two or more of the electrodes to a ventricle of the patient's heart by pacing the bundle of His. A rechargeable power supply is disposed within the housing and is operably coupled to the controller and is configured to supply power to the controller. A loop structure extends from the housing and is convertible between a collapsed configuration for delivery and an expanded configuration for deployment in which the loop structure and the housing fit within the atrium of the patient's heart. The loop structure is configured as a loop antenna having two or more windings for receiving transmitted energy and the controller is further configured to utilize the received transmitted energy to recharge the rechargeable power supply.

Alternatively or additionally, the loop structure may be configured to be situated in a tricuspid valve annulus to help secure the LCP in position relative to the tricuspid valve.

Alternatively or additionally, the controller may be configured to sense activation of the atrium of the patient's heart via two or more of the electrodes, and in response, wait for a period time before delivering a pacing pulse to activate the bundle of His in the patient's atrioventricular septum.

Alternatively or additionally, the LCP may further include one or more fixation elements that are secured relative to the housing and that are configured to fix the LCP relative to the tricuspid valve.

Alternatively or additionally, the loop structure may include one or more fixation features for anchoring the loop structure relative to a tricuspid valve annulus.

Alternatively or additionally, the loop structure may further include a surface treatment configured to encourage endothelialization.

Alternatively or additionally, the loop structure may include a support structure for supporting the two or more windings, wherein the support structure includes a shape memory alloy.

Alternatively or additionally, the LCP may be configured for deployment within a right atrium of the patient's heart and to deliver a pacing pulse to activate the bundle of His in the patient's atrioventricular septum.

In another example, a leadless cardiac pacemaker (LCP) is configured for atrial placement in a patient's tricuspid valve annulus and to provide ventricle pacing via the patient's bundle of His. The LCP includes a housing that is configured for deployment within the right atrium of the patient's heart as well as an energy receiving antenna including a loop structure that is secured relative to the housing. The loop structure is convertible between a collapsed configuration for delivery and an expanded configuration for deployment in which the loop structure fits about the tricuspid valve annulus and helps secure the LCP in position relative to the tricuspid valve. A rechargeable power supply is disposed within the housing. The LCP includes two or more electrodes and a controller that is disposed within the housing and is operably coupled to the energy receiving antenna, the rechargeable power supply and the two or more electrodes. The controller is configured to sense atrial electrical activity via two or more of the electrodes and to provide ventricle pacing by delivering pacing pulses via two or more of the electrodes at an energy level that is sufficient to activate the patient's bundle of His. The controller is also configured to utilize energy received via the energy receiving antenna to recharge the rechargeable power supply.

Alternatively or additionally, the loop structure of the energy receiving antenna may include a shape memory material.

Alternatively or additionally, the LCP may further include one or more fixation elements that are secured relative to the housing and are configured for fixation of the LCP relative to the tricuspid valve.

Alternatively or additionally, the energy receiving antenna may include one or more fixation features for anchoring the energy receiving antenna relative to the tricuspid valve annulus.

Alternatively or additionally, the energy receiving antenna may include a plurality of wire windings suitable for receiving energy.

Alternatively or additionally, the energy receiving antenna may further include a surface treatment to influence endothelialization.

In another example, a leadless cardiac pacemaker (LCP) may be configured for atrial placement. The LCP includes a housing, two or more electrodes and a controller that is disposed within the housing and is operably coupled to the two or more electrodes. The controller is configured to sense activation of the atrium of the patient's heart via two or more of the electrodes and to deliver pacing therapy via two or more of the electrodes to a ventricle of the patient's heart by pacing the bundle of His in the patient's atrioventricular septum.

Alternatively or additionally, the LCP may further include one or more fixation elements that are secured relative to the housing and that are configured to fix the LCP relative to the tricuspid valve of the patient.

Alternatively or additionally, the controller may be configured to deliver pacing therapy by delivering pacing pulses at an energy level that is sufficient to activate the patient's bundle of His.

Alternatively or additionally, the LCP may further include a rechargeable power supply that is disposed within the housing and is operably coupled to the controller, the rechargeable power supply being configured to supply power to the controller. The LCP may further include a loop structure that extends from the housing and is convertible between a collapsed configuration for delivery and an expanded configuration for deployment in which the loop structure is configured to be situated in the annulus of the tricuspid valve to help secure the LCP in position relative to the tricuspid valve, wherein the loop structure is configured as a loop antenna having two or more windings for receiving transmitted energy. The controller is further configured to utilize the received transmitted energy to recharge the rechargeable power supply.

Alternatively or additionally, the loop structure may include one or more fixation features for anchoring the loop structure relative to the tricuspid valve annulus.

Alternatively or additionally, the loop structure may include a support structure for supporting the two or more windings, wherein the support structure includes a shape memory alloy.

The above summary of some illustrative embodiments is not intended to describe each disclosed embodiment or every implementation of the present disclosure. The Figures, and Description, which follow, more particularly exemplify some of these embodiments.

BRIEF DESCRIPTION OF THE DRAWINGS

The disclosure may be more completely understood in consideration of the following description in connection with the accompanying drawings, in which:

FIGS. 3A through 3D are schematic cross-sectional views of illustrative loop structure for use in FIG. 2, taken along line 3-3 of FIG. 2;

FIG. 10 is a schematic block diagram of a leadless cardiac pacemaker (LCP) in accordance with another example of the disclosure.

Figure 1:
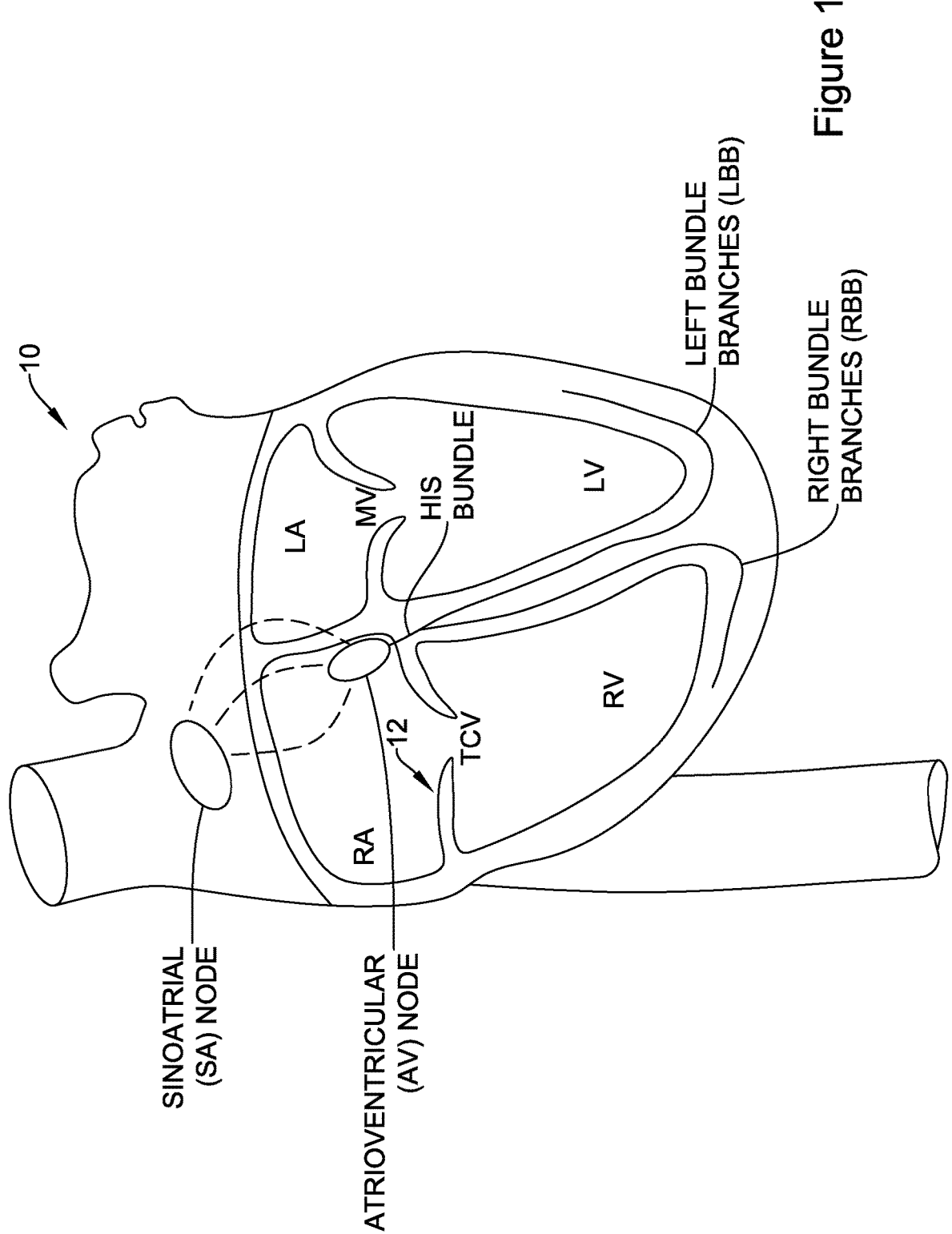
FIG. 1 is a schematic partial cutaway view of a human heart, showing features of the conductive system of the heart.

While the disclosure is amenable to various modifications and alternative forms, specifics thereof have been shown by way of example in the drawings and will be described in detail. It should be understood, however, that the intention is not to limit the disclosure to the particular embodiments described. On the contrary, the intention is to cover all modifications, equivalents, and alternatives falling within the spirit and scope of the disclosure.

DESCRIPTION

For the following defined terms, these definitions shall be applied, unless a different definition is given in the claims or elsewhere in this specification.

All numeric values are herein assumed to be modified by the term "about," whether or not explicitly indicated. The term "about" generally refers to a range of numbers that one of skill in the art would consider equivalent to the recited value (i.e., having the same function or result). In many instances, the terms "about" may include numbers that are rounded to the nearest significant figure.

The recitation of numerical ranges by endpoints includes all numbers within that range (e.g. 1 to 5 includes 1, 1.5, 2, 2.75, 3, 3.80, 4, and 5).

As used in this specification and the appended claims, the singular forms "a", "an", and "the" include plural referents unless the content clearly dictates otherwise. As used in this specification and the appended claims, the term "or" is generally employed in its sense including "and/or" unless the content clearly dictates otherwise.

It is noted that references in the specification to "an embodiment", "some embodiments", "other embodiments", etc., indicate that the embodiment described may include one or more particular features, structures, and/or characteristics. However, such recitations do not necessarily mean that all embodiments include the particular features, structures, and/or characteristics. Additionally, when particular features, structures, and/or characteristics are described in connection with one embodiment, it should be understood that such features, structures, and/or characteristics may also be used connection with other embodiments whether or not explicitly described unless clearly stated to the contrary.

The following detailed description should be read with reference to the drawings in which similar structures in different drawings are numbered the same. The drawings, which are not necessarily to scale, depict illustrative embodiments and are not intended to limit the scope of the disclosure. While the present disclosure is applicable to any suitable implantable medical device (IMD), the description below often uses implantable cardioverter-defibrillator (ICD) and/or pacemakers as particular examples.

FIG. 1 is a schematic illustration of a heart 10, including a right atrium RA, a right ventricle RV, a left atrium LA and a left ventricle LV. In this cutaway view of the heart 10, several of the heart valves can be seen. The heart 10 includes a tricuspid valve TCV that, when open, permits blood to flow from the right atrium RA to the right ventricle RV while preventing blood flowing in a reverse direction. The tricuspid valve TCV includes an annulus 12 that surrounds the tricuspid valve TCV. The heart 10 also includes a mitral valve MV that, when open, permits blood to flow from the left atrium LA to the left ventricle LV while preventing blood flowing in a reverse direction. The other valves of the heart, namely the aortic valve and the pulmonary valve, are not visible in this cutaway.

FIG. 1 also illustrates features of the heart's electrical conductive system. In a healthy heart, the sinoatrial (SA) node, which may be considered as being the heart's natural pacemaker, generates electrical impulses that propagate through the heart's conductive system to various regions of the heart to excite corresponding muscle tissues within the heart 10. Coordinated delays in the propagation of these electrical impulses cause various portions of the heart 10 to contract in synchrony, resulting in efficient pumping. In some cases, blockages or other problems in the heart's electrical conductive system may cause asynchronized contraction of the heart 10, which can result in inefficient pumping, which in turn can impact blood flow to tissues within the body.

In particular, the heart's electrical conduction system includes intermodal pathways between the SA node and the atrioventricular (AV) node, the His Bundle (also known as the Bundle of His, the AV bundle, and the Common bundle), and the Purkinje system including the right bundle branch RBB and the left bundle branch LBB. In the normal heart 10, electrical impulses generated from the SA node are conducted to the right atrium (RA) and the left atrium (LA), resulting in the contraction of the atriums, and also to the AV node through the internodal pathways. The propagation of the electrical impulses is delayed in the AV node. The His Bundle conducts the electrical impulses from the AV node to the right bundle branch RBB and left bundle branch LBB. The right bundle branch RBB and the left bundle branch LBB then conduct the electrical impulses to the right ventricle RV and left ventricle LV, respectively, through the Purkinje system, resulting in the contraction of the ventricles.

When there a problems with the AV node, it will be appreciated that it is feasible to pace both the right ventricle RV and the left ventricle LV in proper synchrony by providing electrical pacing pulses to the His Bundle. As can be seen in FIG. 1, the His Bundle is disposed in the atrioventricular septum which is a portion of the structure (including the atrial septum and the ventricular septum) dividing the heart 10 into a right side and a left side. In some cases, the His Bundle may be paced from a position within the right atrium RA, such as near the tricuspid valve TCV. It will be appreciated that placing an implantable medical device such as but not limited to a leadless cardiac pacemaker (LCP) within the right atrium RA can provide some challenges with respect to the overall dimensions of the LCP. In some cases, there can be challenges in anchoring an LCP within the right atrium. In some cases, pacing the His Bundle can require a relatively higher power level. In some cases, an LCP configured for placement within the right atrium RA and for pacing the His Bundle may include a rechargeable power supply in order to meet the power requirements of His Bundle pacing while also meeting the size limitations resulting from placement within the relatively small right atrium RA. FIGS. 2 through 10 provide a plurality of examples of LCPs that are configured for pacing the His Bundle from within the right atrium RA. In some cases, such a device may be implanted in the left atrium, sometimes in the mitral valve annulus, for pacing the His Bundle from within the left atrium LA. In some cases, pacing the His Bundle may include para-Hisian pacing, which involves pacing distal to the His Bundle but proximal to the right bundle branch RBB.

Figure 2:
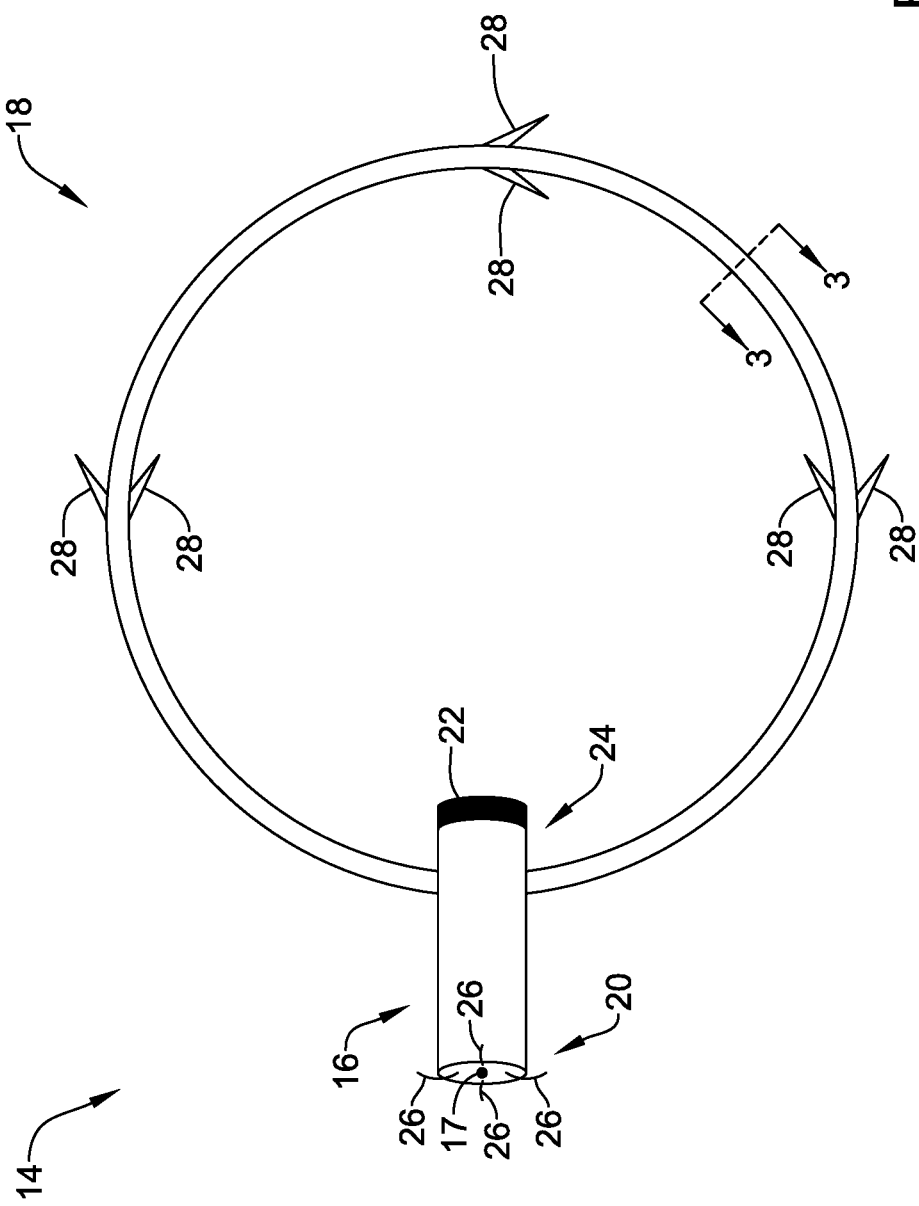
FIG. 2 is a schematic view of a leadless cardiac pacemaker (LCP) in accordance with an example of the disclosure, with a loop structure portion of the LCP shown in an expanded configuration.
Figure 4:
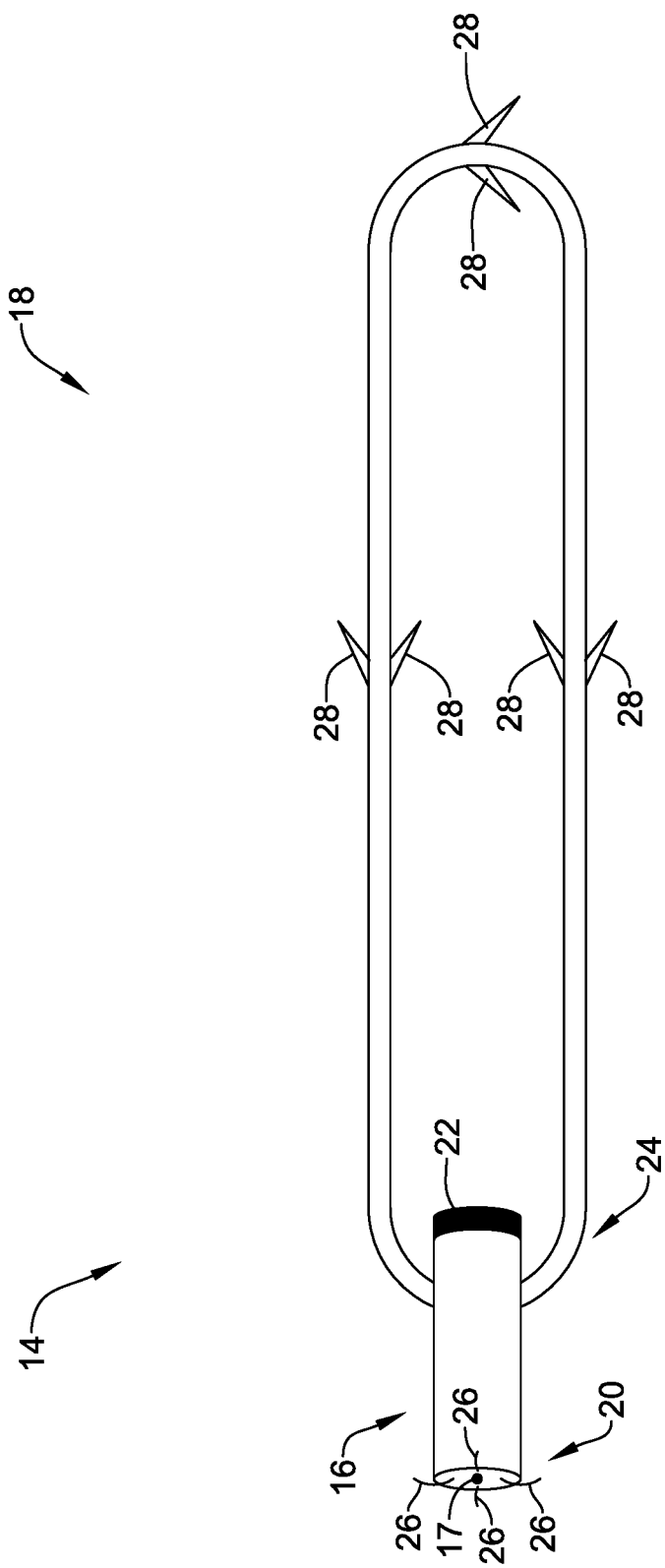
FIG. 4 is a schematic view of the LCP of FIG. 2, with the loop structure portion of the LCP shown in a collapsed configuration for delivery.

FIG. 2 is a schematic view of a leadless cardiac pacemaker (LCP) 14 that includes a housing 16 and a loop antenna 18 extending from the housing 16. FIG. 2 shows the loop antenna 18 in an expanded, or deployed, configuration, while FIG. 4 shows the loop antenna 18 in a collapsed configuration suitable for delivery. The illustrative housing 16 includes a cathode 17 that is disposed at a distal end 20 of the housing 16 and an anode 22 that is disposed at or near a proximal end 24 of the housing 16. In some cases, one or more electrodes may be supported at one or more locations along the loop antenna 18 to help with sensing, pacing and or communication.

In some cases, as illustrated, the LCP 14 may include one or more fixation elements 26, such as fixation tines, extending distally from the distal end 20 of the housing 16. While a total of four fixation times 26 are illustrated, in some cases the LCP 14 may include only one, two or three fixation times 26. In some instances, the LCP 14 may include five or more fixation times 26. In some cases, the LCP 14 may not include any fixation times 26. The fixation times 26 may be beneficial in initially locating and anchoring the LCP 14 within the right atrium RA prior to positioning the loop antenna 18. Rather than fixation tines as shown, it is contemplated that the fixation element(s) 26 may include any suitable fixation structure such as one or more pins, staples, threads, screws, helix, tines, and/or the like.

In some cases, the cathode electrode used for pacing the bundle of His may be positioned on a distal end of a needle, pin or the like, so that the cathode electrode is positioned at a desired depth in the atrioventricular septum and closer to the bundle of His. This may help reduce the energy required to pace the bundle of His. In some cases, the cathode electrode may be positioned on a fixation element, such at or near a distal end of a screw or helix.

The loop antenna 18 may be secured to the housing 16, such as the proximal end 24 of the housing 16. In some cases, as will be discussed, the loop antenna 18 includes a plurality of conductive windings, thereby forming an inductive loop that can be used to receive energy transmitted from a position remote from the LCP 14 (and in some cases, remote from the patient's body) in order to charge a power supply within the LCP 14.

In some cases, the loop antenna 18 may be configured to fit within the annulus 12 (FIG. 1) of the tricuspid valve TCV in order to help secure the LCP 14 in the atrium. In other instances, the loop antenna 18 may be configured to span across the interior of the right atrium RA, and thus can help secure the LCP 14 in position by virtue of the interaction between the loop antenna 18 and the interior surfaces of the right atrium RA. In some cases, the loop antenna 18 may be configured to have a compressive or frictional fit within the atrial appendage (not visible in FIG. 1). In some cases, the loop antenna 18 may include one or more fixation elements 28. While the fixation elements 28 are shown as simple barb shapes, other configurations are contemplated. While a total of three pairs of fixation elements 28 are shown, it will be appreciated that in some cases the loop antenna 18 may not include any fixation elements 28, or may include even more fixation elements 28. While the fixation elements 28 are illustrated as being disposed in pairs, this is not required in all cases. In some cases, one or more fixation elements 28 may be individually arranged about the loop antenna 18. In some instances, at least some of the fixation elements 28 may be arranged in groups of three, four, five or more.

Figure 3B:
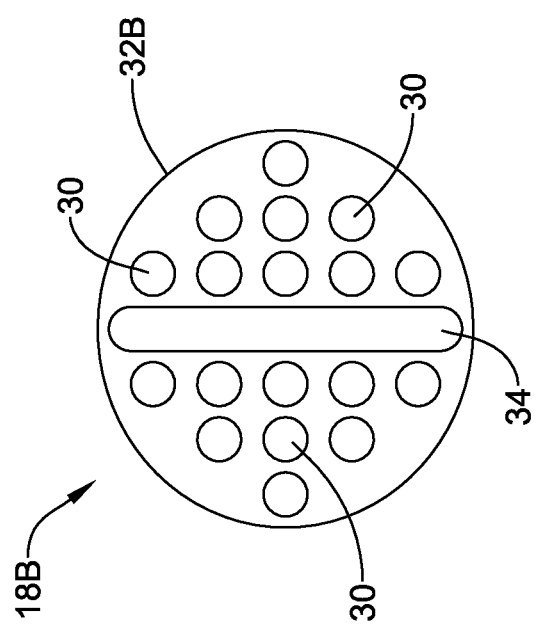
Figure 7:
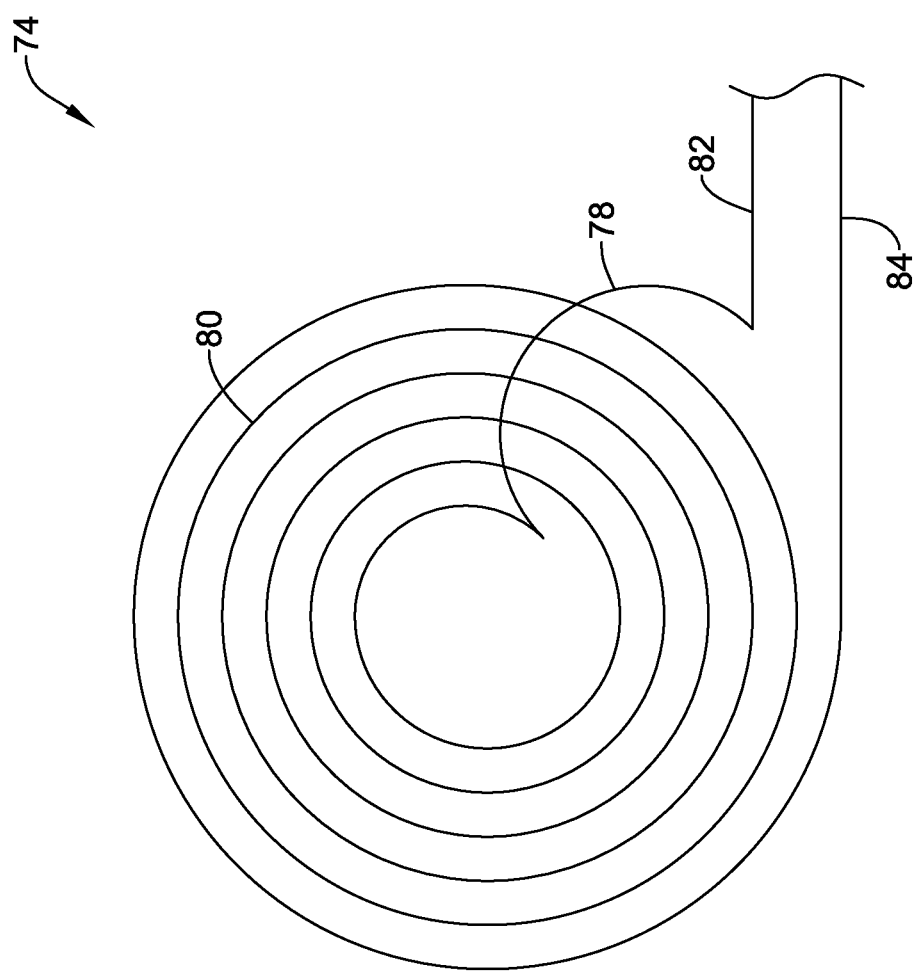
FIG. 7 is a schematic view of an antenna winding forming a portion of the loop structures shown in FIGS. 2 through 6.

FIGS. 3A through 3D show illustrative but non-limiting schematic cross-sectional views of the loop antenna 18, illustrating particular features of the internal structure of the loop antenna 18. Each of these schematic cross-sectional views may be considered as having been taken along line 3-3 of FIG. 2. FIG. 3A shows a cross-section of a loop antenna 18a. It can be seen that the loop antenna 18a includes a plurality of individual conductive windings 30 encapsulated or otherwise contained within a loop housing 32a. The windings 30 may be part of one elongated conductor, such as shown in FIG. 7. FIG. 3B is a schematic cross-sectional view of a loop antenna 18b that also includes the plurality of individual conductive windings 30 that are encapsulated or otherwise contained within a loop housing 32b.

The loop antenna 18b also includes a shaping member 34 that is disposed within or adjacent to the loop housing 32b. In some cases, the shaping member 34 may help the loop antenna 18b move between a collapsed configuration for delivery and an expanded configuration for deployment. In some cases, the shaping member 34 may be formed of or otherwise include a shape memory material. In some instances, the shaping member 34 may be formed of NITINOL®, which is an alloy of nickel and titanium. The loop housing 32a, 32b may simply be a polymeric covering that surrounds the plurality of individual conductive windings 30. In some cases, the loop housing 32a, 32b may be a polymeric encapsulant. In some cases, the loop housing 32a, 32b may be formed of a biocompatible polymeric material that provides the loop antenna 18a with biocompatibility while also protecting the plurality of individual conductive windings 30 from bodily fluids such as blood.

In some cases, as shown for example in FIGS. 3A and 3B, the loop antenna 18 may have a circular or at least substantially circular cross-sectional profile. In some cases, the loop antenna 18 may have an ovoid cross-sectional profile, a rectilinear cross-sectional profile, or any other suitable profile. In some cases, as shown for example in FIGS. 3C and 3D, the loop antenna 18 may have a triangular cross-sectional profile. In some cases, a triangular cross-sectional profile may provide spatial advantages when the loop antenna 18 is in its collapsed, or delivery, configuration, as the loop antenna 18 may better fit against itself when folded or twisted into the collapsed configuration.

Figure 3C:
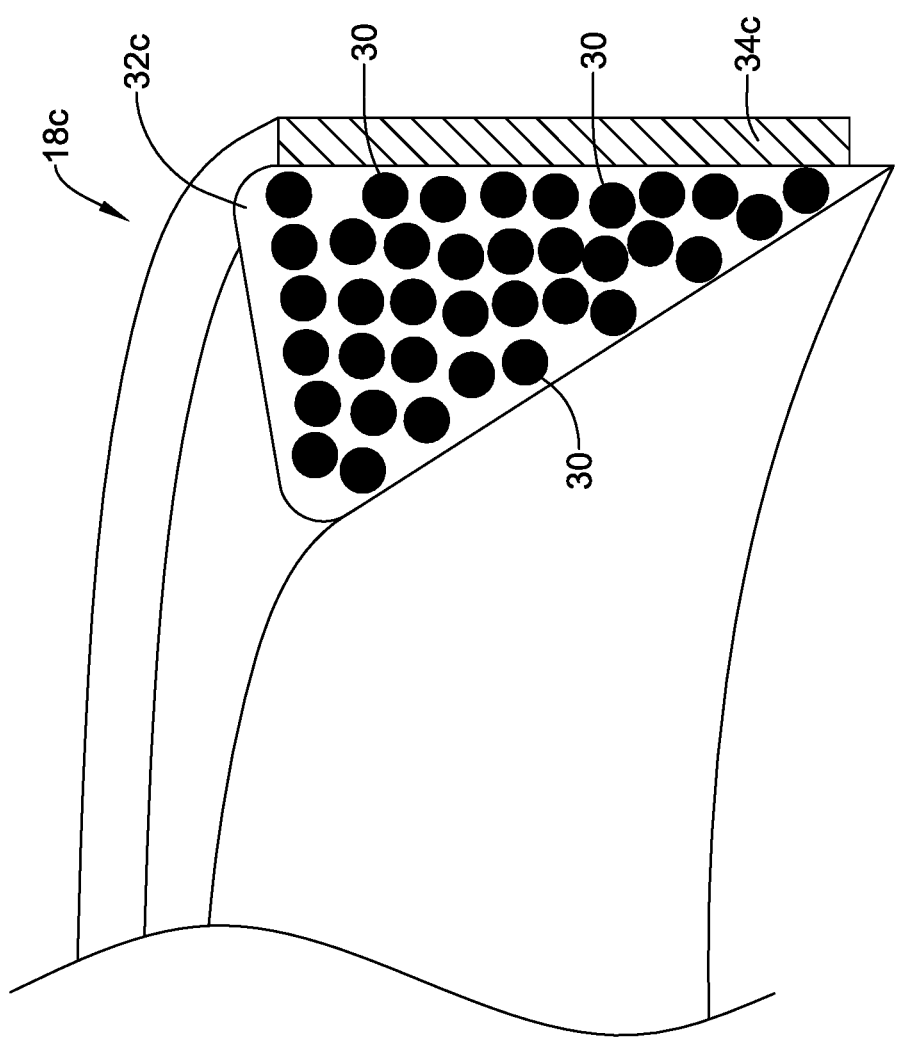
Figure 3D:
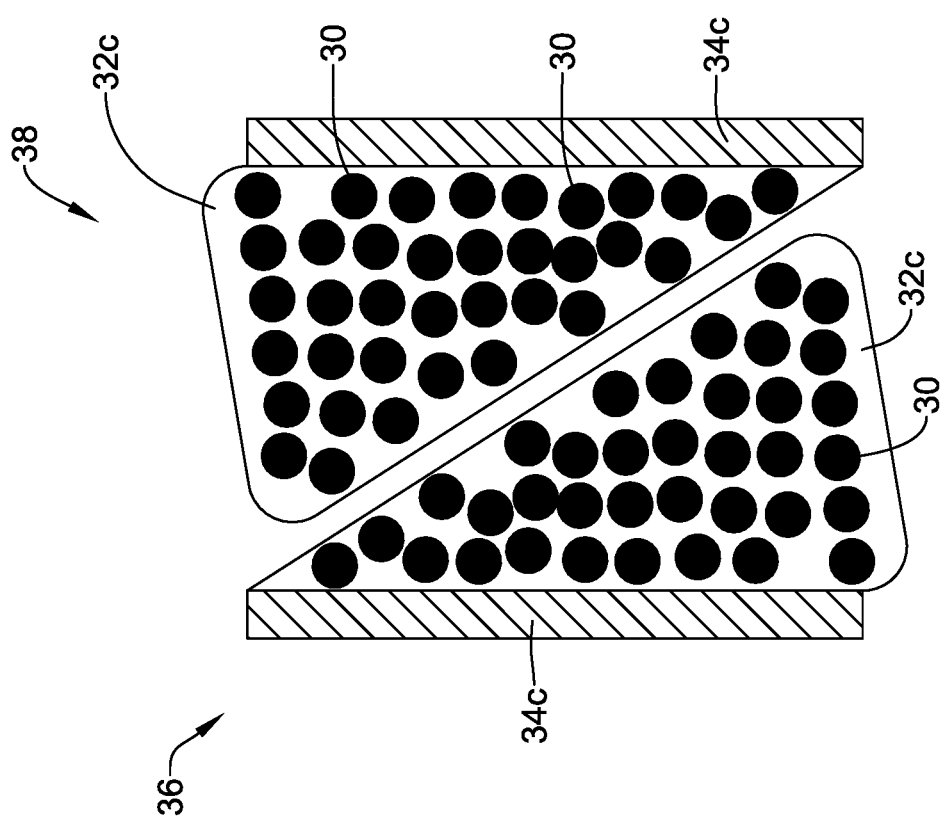

FIG. 3C is a cross-sectional view of a loop antenna 18c that includes a plurality of conductive windings 30 that are encapsulated or otherwise enclosed within a loop housing 32c. In this example, the loop housing 32c has a triangular cross-sectional profile. The loop antenna 18c may, as illustrated, include a shaping member 34c that helps the loop antenna 18c move from a collapsed configuration for delivery to an expanded configuration for deployment. In this example, the shaping member 34c is position along an outwardly facing side of the loop housing 32c and is configured to fit against the tricuspid valve annulus. FIG. 3D illustrates how a first portion 36 of the loop antenna 18c may nest together with a second portion 38 of the loop antenna 18c. In some cases, this may mean that the loop antenna 18c has a collapsed configuration in which there is a twist formed within the loop antenna 18c, somewhere between the first portion 36 of the loop antenna 18c and the second portion 38 of the loop antenna 18c.

Figure 5:
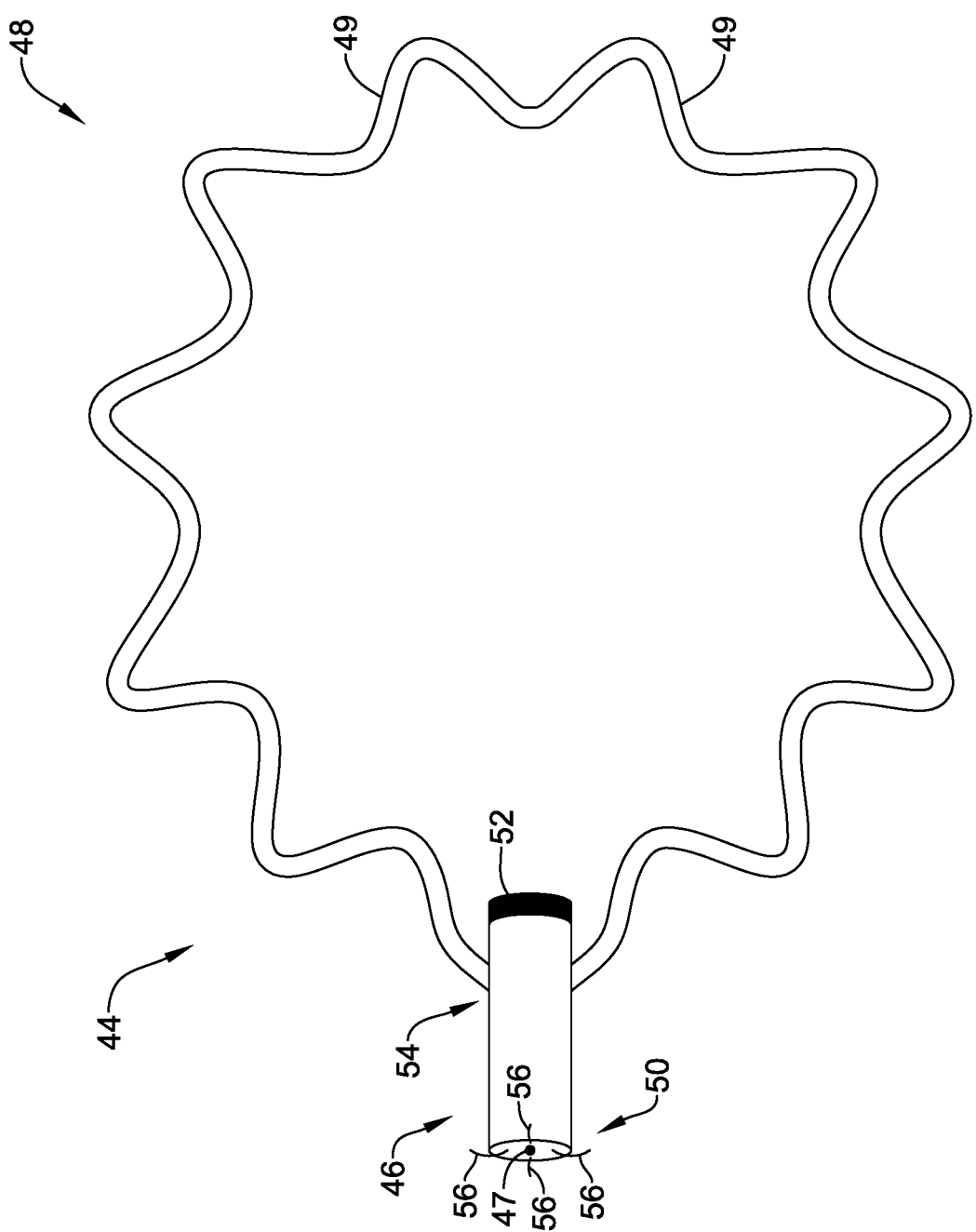
FIG. 5 is a schematic view of a leadless cardiac pacemaker (LCP) in accordance with another example of the disclosure.

FIG. 5 is a schematic view of a leadless cardiac pacemaker (LCP) 44 that includes a housing 46 and a loop antenna 48 extending from the housing 46. The illustrative housing 46 includes a cathode 47 that is disposed at a distal end 50 of the housing 46 and an anode 52 that is disposed at or near a proximal end 54 of the housing 46. In some cases, as illustrated, the LCP 44 may include one or more fixation elements 56, such as fixation tines, extending distally from the distal end 50 of the housing 46. While a total of four fixation elements 56 are illustrated, in some cases the LCP 44 may include only one, two or three fixation elements 56. In some instances, the LCP 44 may include five or more fixation elements 56. In some cases, the LCP 44 may not include any fixation elements 56. The fixation elements 56 may be beneficial in initially locating and anchoring the LCP 44 within the right atrium RA (such as in the tricuspid valve atrium) prior to positioning the loop antenna 48.

The loop antenna 48 may be secured at either end of the loop antenna 48 to the housing 46. In some cases, as will be discussed, the loop antenna 48 may include a plurality of conductive windings, thereby forming an inductive loop that can be used to receive energy transmitted from a position remote from the LCP 44 in order to charge a power supply within the LCP 44. In some cases, the loop antenna may also be used for one-way or bi-directional communication with a remote device.

In some cases, the loop antenna 48 may be configured to fit within the annulus 12 (FIG. 1) of the tricuspid valve TCV in order to help secure the LCP 44 relative to the atrium. In some instances, the loop antenna 48 may be configured to span across the interior of the right atrium RA, and thus can help secure the LCP 44 in position by virtue of the interaction between the loop antenna 48 and the interior surfaces of the right atrium RA. In some cases, the loop antenna 48 may be configured to have a compressive or frictional fit within the atrial appendage (not visible in FIG. 1). In some cases, the loop antenna 48 may be considered as being highly compliant, and may for example be sufficiently conformable to be considered as providing a "one size fits all" approach, and thus a single size loop antenna 48 may be able to be used in a variety of different patients hearts, and may be able to be used to anchor the LCP 44 by interacting with various portions of the interior of the patient's heart. The loop antenna 48 may, as illustrated, be configured to include a number of undulations 49 that help the loop antenna 48 accommodate various size atriums. While not shown, in some cases, the loop antenna 48 may include one or more fixation features such as the fixation elements 28 shown in FIGS. 2 and 3.

Figure 6:
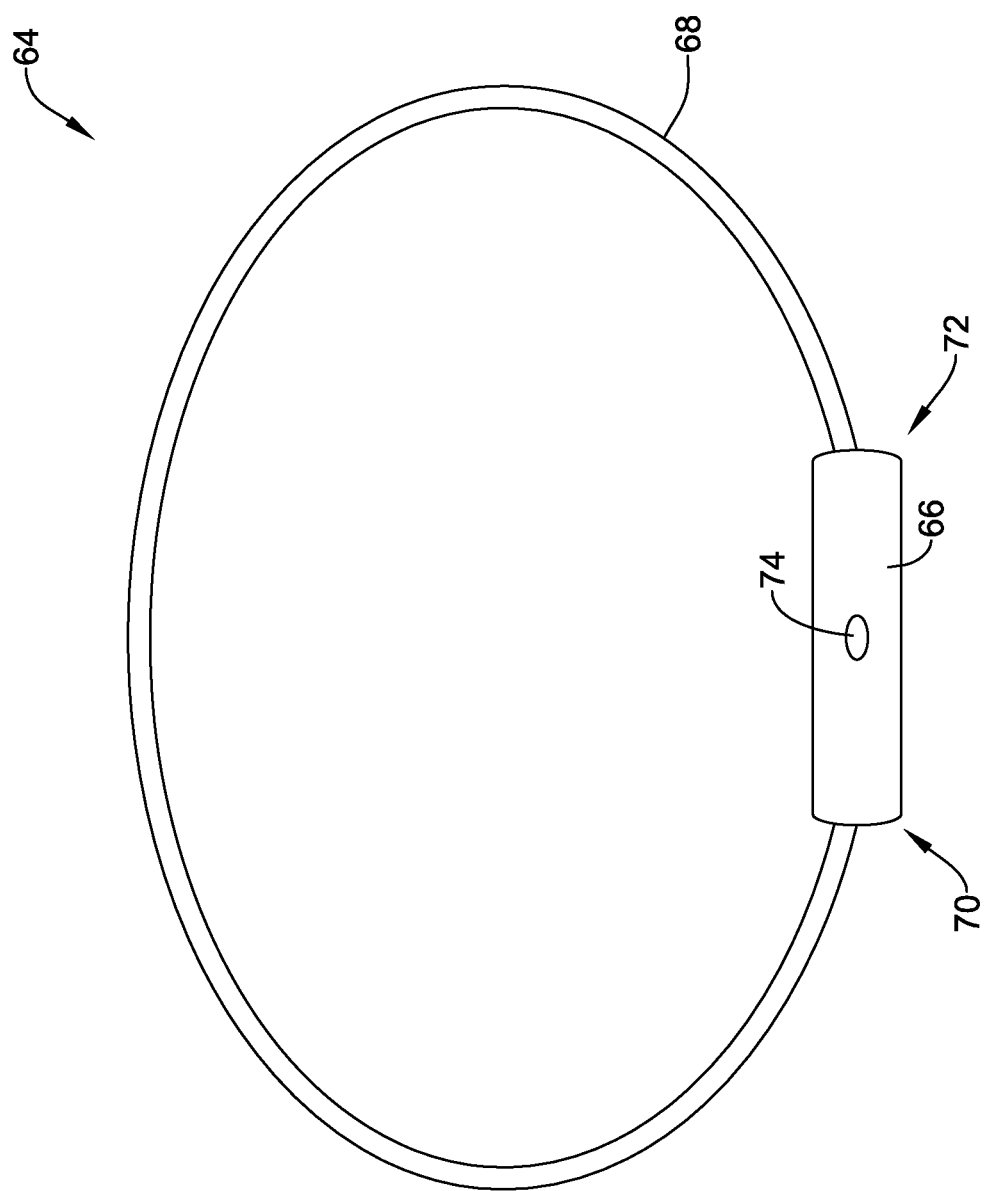
FIG. 6 is a schematic view of a leadless cardiac pacemaker (LCP) in accordance with another example of the disclosure.

FIG. 6 is a schematic view of a leadless cardiac pacemaker (LCP) 64 that includes a housing 66 and a loop antenna 68 extending from the housing 66. Unlike the LCP 14 or the LCP 44 shown in previous Figures, where the loop antenna 18 or 48 was shown with both leads of the loop antenna 18, 48 extending from a single end of the housing 16, 46, the LCP 64 of FIG. 6 is configured with one lead of the loop antenna 68 extending from a distal end 70 of the housing 66 and the other lead of the loop antenna 68 extending from a proximal end 72 of the housing 66. In some cases, this configuration may be beneficial for disposing the LCP 64 within the annulus 12 of the tricuspid valve TCV. It will be appreciated that the loop antenna 68 is shown in an expanded, or deployed, configuration, and may be collapsed into a collapsed configuration for delivery. In the illustrative embodiment, the housing 46 includes a cathode 74 that is visible, and an anode that is not visible in the illustrated orientation. In some cases, as will be discussed, the loop antenna 68 includes a plurality of conductive windings, thereby forming an inductive loop that can be used to receive energy transmitted from a position remote from the LCP 64 in order to charge a power supply within the LCP 64 (and/or for communication).

FIG. 7 is a schematic view of an inductive loop 76 in which a single conductive member 78 is wound into a plurality of loops 80. The inductive loop 76 may be considered as an example of an inductive loop that may form a portion of the loop antenna 18, 18a, 18b, 18c, 48, 68 shown in previous Figures. The single conductive member 78 has a first end 82 and a second end 84, which may be coupled to circuitry within the LCP 14, 44, 64, for example. The first end 82 and the second end 84 may both enter at one end of the LCP 14, 44, as shown for example in FIGS. 2 and 5, or may enter at opposing ends of the LCP 64, as shown for example in FIG. 6. The conductive member 78 may be formed of any suitable conductive material, although in some cases the conductive member 78 may be formed of platinum, palladium, aluminum, copper, and/or gold.

Figure 8:
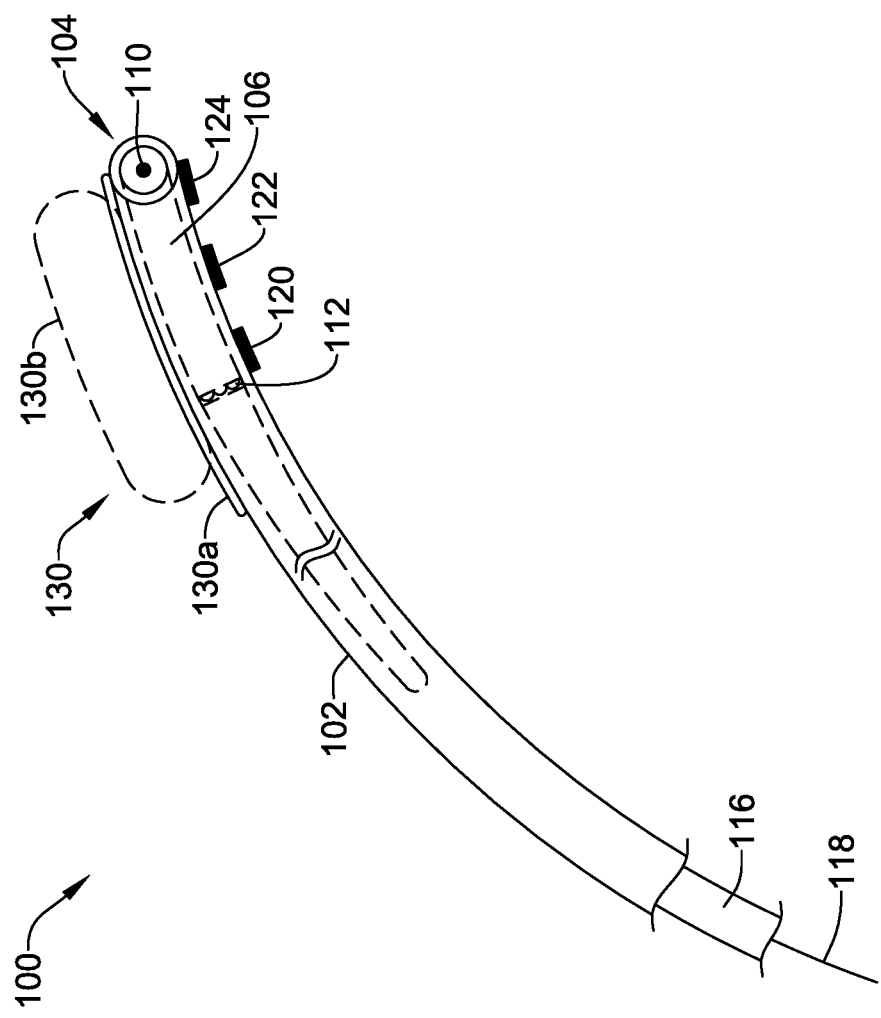
FIG. 8 is a schematic view of the LCP of FIG. 2 shown disposed within a delivery catheter in accordance with an example of the disclosure.

In some cases, the LCP 14, 44, 64 described herein may be delivered transvascularly. FIG. 8 shows an illustrative but non-limiting example of a delivery device 100 that may be used to deliver the LCP 14, 44, 64. The delivery device 100 includes an outer sheath 102 defining an interior lumen 104 that is dimensioned to accommodate an LCP 106, shown in phantom. The LCP 106 may be considered as representing the LCP 14, 44, 64, for example, and includes a housing 108 bearing a cathode 110 (visible through the end of the outer sheath 102) and an anode 112. A loop antenna 114 extends proximally from the housing 108. In the example show, the delivery device 100 includes a pusher tube 116 that is slidingly disposed within the interior lumen 104 of the outer sheath 102, and is configured to be able to push against the LCP 106. A tether 118 extends within the pusher tube 116, and is releasably engaged with the LCP 106. As a result, the pusher tube 116 and the tether 118 may be used, in combination, to either urge the LCP 106 forward, out of the interior lumen 104 of the outer sheath 102, or to retract the LCP 106 back into the interior lumen 104 of the outer sheath 102.

In some cases, the outer sheath 102 of the delivery device 100 may include one or several electrodes that may be used to test a particular site for suitability before deploying the LCP 106. As illustrated, the delivery device 100 includes three electrodes 120, 122 and 124, although in some cases fewer electrodes may be used. In some cases, additional electrodes may be disposed on the outer sheath 102 in order to provide a sort of mapping functionality, for example. In some cases, depending on the telemetry capabilities of the LCP 106, the cathode 110 of the LCP 106 may also be used for testing a particular site for suitability before deploying the LCP 106. In some cases, the delivery device 100 includes a balloon 130 that may be inflated to help push the electrodes 120, 122, 124 into contact with tissue at a particular site. In some cases, the balloon 130 has a deflated configuration, shown as solid line 130*a*, and an inflated configuration, shown as dashed line 130*b*.

Figure 9:
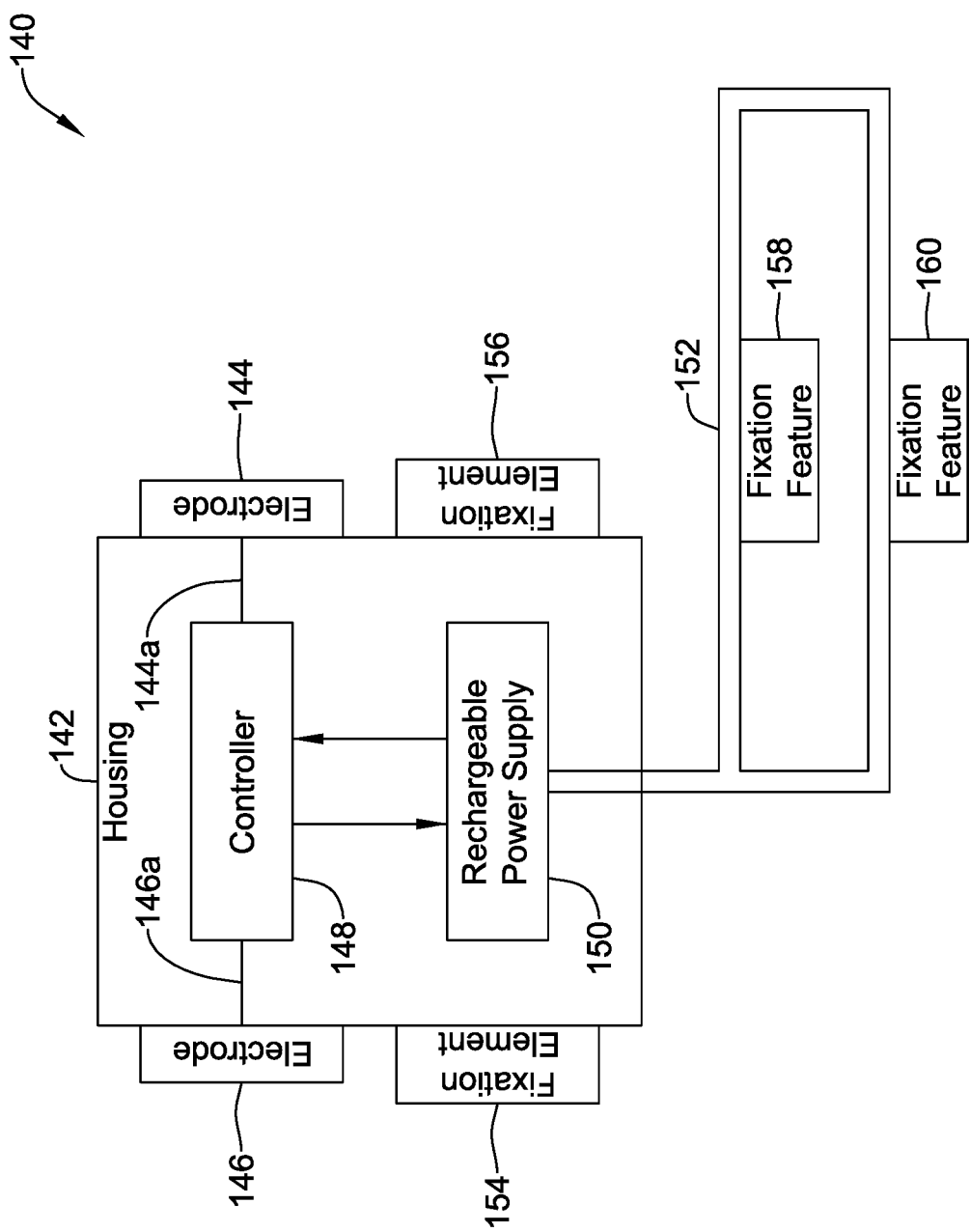
FIG. 9 is a schematic block diagram of a leadless cardiac pacemaker (LCP) in accordance with an example of the disclosure.

FIG. 9 is a schematic block diagram of a leadless cardiac pacemaker (LCP) 140 that may be considered as being an example of the LCPs 14, 44, 64 and 106 discussed previously. The LCP 140 may be configured for placement within the patient's atrium, such as the right atrium RA, and may include a housing 142 and electrodes 144, 146 that are disposed relative to the housing 142. While two electrodes 144, 146 are shown, in some cases the LCP 140 may include three or more electrodes. A controller 148 is disposed within the housing 142 and is operably coupled to the electrodes 144, 146 via electrical connections 144*a* and 146*a*, respectively.

The controller 148 may be configured to deliver pacing therapy via the electrodes 144, 146 to a ventricle of the patient's heart by pacing the bundle of His. In some cases, the controller 148 may be configured to sense activation of the atrium of the patient's heart via the electrodes 144, 146, and in response, wait for a period time (e.g. AV delay) before delivering a pacing pulse to activate the bundle of His in the patient's atrioventricular septum. In some cases, the LCP 140 may be configured for deployment within the right atrium RA and may be configured to deliver a pacing pulse to activate the bundle of His in the patient's atrioventricular septum. In some instances, the LCP 140 may be configured to deliver a pacing pulse with sufficient energy to activate the bundle of His. The illustrative LCP 140 includes a rechargeable power supply 150 that is disposed within the housing 142 and that is operably coupled to the controller 148 such that the rechargeable power supply 150 is able to supply power to the controller 148.

The illustrative LCP 140 includes a loop structure 152 that extends from the housing 142 and that is convertible between a collapsed configuration for delivery and an expanded configuration (as illustrated) for deployment in which the loop structure 152 and the housing 142 fit within the atrium of the patients heart. In some cases, the loop structure 152 is configured as a loop antenna having two or more windings for receiving transmitted energy, and the controller 148 may be configured to utilize the received transmitted energy to recharge the rechargeable power supply 150. In some cases, the LCP 140 further includes fixation elements 154 and 156 that are secured relative to the housing 142. In some cases, the fixation elements 154, 156, which are shown schematically, may be configured to help fix the LCP 140 relative to the tricuspid valve TCV.

In some cases, the loop structure 152 may be configured to be situated in a tricuspid valve annulus 12 (FIG. 1) in order to help secure the LCP 140 in position relative to the atrium. In some cases, the loop structure 152 may include one or more fixation features 158, 160 for anchoring the loop structure 152 relative to the annulus 12 of the tricuspid valve TCV. While a pair of fixation features 158, 160 are shown, in some cases there may be no fixation features, or there may be three or more fixation features. In some cases, the loop structure 152 may include a surface treatment that is configured to encourage endothelialization. In some cases, as shown for example in previous Figures, the loop structure 152 may include a two or more windings, and a shape memory alloy support structure that supports the two or more windings.

FIG. 10 depicts an illustrative leadless cardiac pacemaker (LCP) that may be implanted into a patient and may operate to deliver appropriate therapy to the heart, such as to deliver anti-tachycardia pacing (ATP) therapy, cardiac resynchronization therapy (CRT), bradycardia therapy, and/or the like. As can be seen in FIG. 10, the LCP 200 may be a compact device with all components housed within the or directly on a housing 220. In some cases, the LCP 200 may be considered as being an example of the LCP 14 (FIG. 2), the LCP 44 (FIG. 5), the LCP 64 (FIG. 6), the LCP 106 (FIG. 8) or the LCP 140 (FIG. 9). In the example shown in FIG. 10, the LCP 200 may include a communication module 202, a pulse generator module 204, an electrical sensing module 206, a mechanical sensing module 208, a processing module 210, a power supply 212, and an electrode arrangement 214. The LCP 200 may also include a loop antenna 232 for receiving inductive power, and a recharge circuit in the power module 230 for recharging the power supply 212 (e.g. battery or capacitor) using the received inductive power. It is contemplated that the LCP 200 may include more or fewer modules, depending on the application.

The communication module 202 may be configured to communicate with devices such as sensors, other medical devices such as an SICD, another LCP, and/or the like, that are located externally to the LCP 200. Such external devices may be located either external or internal to the patient's body. Irrespective of the location, external devices (i.e. external to the LCP 200 but not necessarily external to the patient's body) can communicate with the LCP 200 via communication module 202 to accomplish one or more desired functions. For example, the LCP 200 may communicate information, such as sensed electrical signals, data, instructions, messages, R-wave detection markers, etc., to an external medical device (e.g. SICD and/or programmer) through the communication module 202. The external medical device may use the communicated signals, data, instructions, messages, R-wave detection markers, etc., to perform various functions, such as determining occurrences of arrhythmias, delivering electrical stimulation therapy, storing received data, and/or performing any other suitable function. The LCP 200 may additionally receive information such as signals, data, instructions and/or messages from the external medical device through the communication module 202, and the LCP 200 may use the received signals, data, instructions and/or messages to perform various functions, such as determining occurrences of arrhythmias, delivering electrical stimulation therapy, storing received data, and/or performing any other suitable function. The communication module 202 may be configured to use one or more methods for communicating with external devices. For example, the communication module 202 may communicate via radiofrequency (RF) signals, inductive coupling, optical signals, acoustic signals, conducted communication signals, and/or any other signals suitable for communication.

In the example shown in FIG. 10, the pulse generator module 204 may be electrically connected to the electrodes 214. In some examples, the LCP 200 may additionally include electrodes 214'. In such examples, the pulse generator 204 may also be electrically connected to the electrodes 214'. The pulse generator module 204 may be configured to generate electrical stimulation signals. For example, the pulse generator module 204 may generate and deliver electrical stimulation signals by using energy stored in the power supply 212 within the LCP 200 and deliver the generated electrical stimulation signals via the electrodes 214 and/or 114'. Alternatively, or additionally, the pulse generator 204 may include one or more capacitors, and the pulse generator 204 may charge the one or more capacitors by drawing energy from the power supply 212. The pulse generator 204 may then use the energy of the one or more capacitors to deliver the generated electrical stimulation signals via the electrodes 214 and/or 214'. In at least some examples, the pulse generator 204 of the LCP 200 may include switching circuitry to selectively connect one or more of the electrodes 214 and/or 114' to the pulse generator 204 in order to select which of the electrodes 214/114' (and/or other electrodes) the pulse generator 204 delivers the electrical stimulation therapy. The pulse generator module 204 may generate and deliver electrical stimulation signals with particular features or in particular sequences in order to provide one or multiple of a number of different stimulation therapies. For example, the pulse generator module 204 may be configured to generate electrical stimulation signals to provide electrical stimulation therapy to combat bradycardia, tachycardia, cardiac synchronization, bradycardia arrhythmias, tachycardia arrhythmias, fibrillation arrhythmias, cardiac synchronization arrhythmias and/or to produce any other suitable electrical stimulation therapy. Some more common electrical stimulation therapies include anti-tachycardia pacing (ATP) therapy, cardiac resynchronization therapy (CRT), and cardioversion/defibrillation therapy. In some cases, the pulse generator 204 may provide a controllable pulse energy. In some cases, the pulse generator 204 may allow the controller to control the pulse voltage, pulse width, pulse shape or morphology, and/or any other suitable pulse characteristic.

In some examples, the LCP 200 may include an electrical sensing module 206, and in some cases, a mechanical sensing module 208. The electrical sensing module 206 may be configured to sense the cardiac electrical activity of the heart. For example, the electrical sensing module 206 may be connected to the electrodes 214/214', and the electrical sensing module 206 may be configured to receive cardiac electrical signals conducted through the electrodes 214/214'. The cardiac electrical signals may represent local information from the chamber in which the LCP 200 is implanted. For instance, if the LCP 200 is implanted within an atrium of the heart (e.g. RA, LA), cardiac electrical signals sensed by the LCP 200 through the electrodes 214/214' may represent atrial (or ventricle) cardiac electrical signals.

The mechanical sensing module 208 may include one or more sensors, such as an accelerometer, a pressure sensor, a heart sound sensor, a blood-oxygen sensor, a chemical sensor, a temperature sensor, a flow sensor and/or any other suitable sensors that are configured to measure one or more mechanical/chemical parameters of the patient. Both the electrical sensing module 206 and the mechanical sensing module 208 may be connected to a processing module 210, which may provide signals representative of the sensed mechanical parameters. Although described with respect to FIG. 10 as separate sensing modules, in some cases, the electrical sensing module 206 and the mechanical sensing module 208 may be combined into a single sensing module, as desired.

The electrodes 214/214' can be secured relative to the housing 220 but exposed to the tissue and/or blood surrounding the LCP 200. In some cases, the electrodes 214 may be generally disposed on either end of the LCP 200 and may be in electrical communication with one or more of the modules 202, 204, 206, 208, and 210. The electrodes 214/214' may be supported by the housing 220, although in some examples, the electrodes 214/214' may be connected to the housing 220 through short connecting wires such that the electrodes 214/214' are not directly secured relative to the housing 220. In examples where the LCP 200 includes one or more electrodes 214', the electrodes 214' may in some cases be disposed on the sides of the LCP 200, which may increase the number of electrodes by which the LCP 200 may sense cardiac electrical activity, deliver electrical stimulation and/or communicate with an external medical device. In some cases, one or more of the electrodes 214/214' may be disposed on the loop antenna 232. The electrodes 214/214' can be made up of one or more biocompatible conductive materials such as various metals or alloys that are known to be safe for implantation within a human body. In some instances, the electrodes 214/214' connected to the LCP 200 may have an insulative portion that electrically isolates the electrodes 214/214' from adjacent electrodes, the housing 220, and/or other parts of the LCP 200. In some cases, one or more of the electrodes 214/214' may be provided on a tail (not shown) that extends away from the housing 220.

The processing module 210 can be configured to control the operation of the LCP 200. For example, the processing module 210 may be configured to receive electrical signals from the electrical sensing module 206 and/or the mechanical sensing module 208. Based on the received signals, the processing module 210 may determine, for example, abnormalities in the operation of the heart H. Based on any determined abnormalities, the processing module 210 may control the pulse generator module 204 to generate and deliver electrical stimulation in accordance with one or more therapies to treat the determined abnormalities. The processing module 210 may further receive information from the communication module 202. In some examples, the processing module 210 may use such received information to help determine whether an abnormality is occurring, determine a type of abnormality, and/or to take particular action in response to the information. The processing module 210 may additionally control the communication module 202 to send/receive information to/from other devices using one or more of the electrodes 214/241' and/or the loop antenna 232.

In some examples, the processing module 210 may include a pre-programmed chip, such as a very-large-scale integration (VLSI) chip and/or an application specific integrated circuit (ASIC). In such embodiments, the chip may be pre-programmed with control logic in order to control the operation of the LCP 200. By using a pre-programmed chip, the processing module 210 may use less power than other programmable circuits (e.g. general purpose programmable microprocessors) while still being able to maintain basic functionality, thereby potentially increasing the battery life of the LCP 200. In other examples, the processing module 210 may include a programmable microprocessor. Such a programmable microprocessor may allow a user to modify the control logic of the LCP 200 even after implantation, thereby allowing for greater flexibility of the LCP 200 than when using a pre-programmed ASIC. In some examples, the processing module 210 may further include a memory, and the processing module 210 may store information on and read information from the memory. In other examples, the LCP 200 may include a separate memory (not shown) that is in communication with the processing module 210, such that the processing module 210 may read and write information to and from the separate memory.

The power supply 212 may provide power to the LCP 200 for its operations. In some examples, the power supply 212 may be a rechargeable battery. In other examples, the power supply 212 may be a non-rechargeable battery made of lithium or other suitable materials, as desired. Because the LCP 200 is an implantable device, access to the LCP 200 may be limited after implantation. Accordingly, it is desirable to have sufficient battery capacity to deliver therapy over a period of treatment such as days, weeks, months, years or even decades. The LCP 200 may include a power module 230 that is configured to receive transmitted energy received by the loop antenna 232. In some cases, the LCP 200 may include a pair of feedthroughs 234 and 236 that enable the loop antenna 232 to be electrically coupled with the power module 230. The power module 230 may be configured to receive the transmitted energy from the loop antenna 232 and convert the transmitted energy into a form that can be used for recharging the power supply 212.

To implant the LCP 200 inside a patient's body, an operator (e.g., a physician, clinician, etc.), may fix the LCP 200 to the cardiac tissue of the patient's heart. To facilitate fixation, the LCP 200 may include one or more anchors 216. The anchor 216 may include any one of a number of fixation or anchoring mechanisms. For example, the anchor 216 may include one or more pins, staples, threads, screws, helix, tines, and/or the like. In some examples, although not shown, the anchor 216 may include threads on its external surface that may run along at least a partial length of the anchor 216. The threads may provide friction between the cardiac tissue and the anchor to help fix the anchor 216 within the cardiac tissue. In other examples, the anchor 216 may include other structures such as barbs, spikes, or the like to facilitate engagement with the surrounding cardiac tissue.

In some cases, the cathode electrode used for pacing the bundle of His may be positioned on a distal end of a needle, pin or the like, so that the cathode electrode is positioned at a desired depth in the atrioventricular septum and closer to the bundle of His. This may help reduce the energy required to pace the bundle of His. In some cases, the cathode electrode may be positioned on a fixation element, such at or near a distal end of a screw or helix.

In some cases, implanting the LCP 200 may include disposing the loop antenna 232 in a desired location within the right atrium RA. For example, in some cases, the loop antenna 232 may be configured to have an expanded configuration in which the loop antenna 232 fits into the annulus 12 of the tricuspid valve TCV, thereby securing the LCP 200 in position relative to the atrioventricular septum and thus relative to the His Bundle. In some instances, the loop antenna 232 has an expanded configuration in which the loop antenna 232 spans the interior space of the right atrium RA, or even fits into an atrial appendage, if present.

Various portions of the devices described herein may be made from a metal, metal alloy, polymer (some examples of which are disclosed below), a metal-polymer composite, ceramics, combinations thereof, and the like, or other suitable material. Some examples of suitable metals and metal alloys include stainless steel, such as 304V, 304L, and 316LV stainless steel; mild steel; nickel-titanium alloy such as linear-elastic and/or super-elastic nitinol; other nickel alloys such as nickel-chromium-molybdenum alloys (e.g., UNS: N06625 such as INCONEL® 625, UNS: N06022 such as HASTELLOY® C-22®, UNS: N10276 such as HASTELLOY® C276®, other HASTELLOY® alloys, and the like), nickel-copper alloys (e.g., UNS: N04400 such as MONEL® 400, NICKELVAC® 400, NICORROS® 400, and the like), nickel-cobalt-chromium-molybdenum alloys (e.g., UNS: R30035 such as MP35-N® and the like), nickel-molybdenum alloys (e.g., UNS: N10665 such as HASTELLOY® ALLOY B2®), other nickel-chromium alloys, other nickel-molybdenum alloys, other nickel-cobalt alloys, other nickel-iron alloys, other nickel-copper alloys, other nickel-tungsten or tungsten alloys, and the like; cobalt-chromium alloys; cobalt-chromium-molybdenum alloys (e.g., UNS: R30003 such as ELGILOY®, PHYNOX®, and the like); platinum enriched stainless steel; titanium; combinations thereof; and the like; or any other suitable material.

As alluded to herein, within the family of commercially available nickel-titanium or nitinol alloys, is a category designated "linear elastic" or "non-super-elastic" which, although may be similar in chemistry to conventional shape memory and super elastic varieties, may exhibit distinct and useful mechanical properties. Linear elastic and/or non-super-elastic nitinol may be distinguished from super elastic nitinol in that the linear elastic and/or non-super-elastic nitinol does not display a substantial "superelastic plateau" or "flag region" in its stress/strain curve like super elastic nitinol does. Instead, in the linear elastic and/or non-super-elastic nitinol, as recoverable strain increases, the stress continues to increase in a substantially linear, or a somewhat, but not necessarily entirely linear relationship until plastic deformation begins or at least in a relationship that is more linear that the super elastic plateau and/or flag region that may be seen with super elastic nitinol. Thus, for the purposes of this disclosure linear elastic and/or non-super-elastic nitinol may also be termed "substantially" linear elastic and/or non-super-elastic nitinol.

In some cases, linear elastic and/or non-super-elastic nitinol may also be distinguishable from super elastic nitinol in that linear elastic and/or non-super-elastic nitinol may accept up to about 2-5% strain while remaining substantially elastic (e.g., before plastically deforming) whereas super elastic nitinol may accept up to about 8% strain before plastically deforming. Both of these materials can be distinguished from other linear elastic materials such as stainless steel (that can also can be distinguished based on its composition), which may accept only about 0.2 to 0.44 percent strain before plastically deforming.

In some embodiments, the linear elastic and/or non-super-elastic nickel-titanium alloy is an alloy that does not show any martensite/austenite phase changes that are detectable by differential scanning calorimetry (DSC) and dynamic metal thermal analysis (DMTA) analysis over a large temperature range. For example, in some embodiments, there may be no martensite/austenite phase changes detectable by DSC and DMTA analysis in the range of about −60 degrees Celsius (° C.) to about 120° C. in the linear elastic and/or non-super-elastic nickel-titanium alloy. The mechanical bending properties of such material may therefore be generally inert to the effect of temperature over this very broad range of temperature. In some embodiments, the mechanical bending properties of the linear elastic and/or non-super-elastic nickel-titanium alloy at ambient or room temperature are substantially the same as the mechanical properties at body temperature, for example, in that they do not display a super-elastic plateau and/or flag region. In other words, across a broad temperature range, the linear elastic and/or non-super-elastic nickel-titanium alloy maintains its linear elastic and/or non-super-elastic characteristics and/or properties.

In some embodiments, the linear elastic and/or non-super-elastic nickel-titanium alloy may be in the range of about 50 to about 60 weight percent nickel, with the remainder being essentially titanium. In some embodiments, the composition is in the range of about 54 to about 57 weight percent nickel. One example of a suitable nickel-titanium alloy is FHP-NT alloy commercially available from Furukawa Techno Material Co. of Kanagawa, Japan. Some examples of nickel titanium alloys are disclosed in U.S. Pat. Nos. 5,238,004 and 6,508,803, which are incorporated herein by reference. Other suitable materials may include ULTANIUM™ (available from Neo-Metrics) and GUM METAL™ (available from Toyota). In some other embodiments, a superelastic alloy, for example a superelastic nitinol can be used to achieve desired properties.

A variety of polymeric materials may also be used. Some examples of suitable polymers may include polytetrafluoroethylene (PTFE), ethylene tetrafluoroethylene (ETFE), fluorinated ethylene propylene (FEP), polyoxymethylene (POM, for example, DELRIN® available from DuPont), polyether block ester, polyurethane (for example, Polyurethane 85A), polypropylene (PP), polyvinylchloride (PVC), polyether-ester (for example, ARNITEL® available from DSM Engineering Plastics), ether or ester based copolymers (for example, butylene/poly(alkylene ether) phthalate and/or other polyester elastomers such as HYTREL® available from DuPont), polyamide (for example, DURETHAN® available from Bayer or CRISTAMID® available from Elf Atochem), elastomeric polyamides, block polyamide/ethers, polyether block amide (PEBA, for example available under the trade name PEBAX®), ethylene vinyl acetate copolymers (EVA), silicones, polyethylene (PE), Marlex high-density polyethylene, Marlex low-density polyethylene, linear low density polyethylene (for example REXELL®), polyester, polybutylene terephthalate (PBT), polyethylene terephthalate (PET), polytrimethylene terephthalate, polyethylene naphthalate (PEN), polyetheretherketone (PEEK), polyimide (PI), polyetherimide (PEI), polyphenylene sulfide (PPS), polyphenylene oxide (PPO), poly paraphenylene terephthalamide (for example, KEVLAR®), polysulfone, nylon, nylon-12 (such as GRILAMID® available from EMS American Grilon), perfluoro(propyl vinyl ether) (PFA), ethylene vinyl alcohol, polyolefin, polystyrene, epoxy, polyvinylidene chloride (PVdC), poly(styrene-b-isobutylene-b-styrene) (for example, SIBS and/or SIBS 50A), polycarbonates, ionomers, biocompatible polymers, other suitable materials, or mixtures, combinations, copolymers thereof, polymer/metal composites, and the like. In some embodiments the sheath can be blended with a liquid crystal polymer (LCP). For example, the mixture can contain up to about 6 percent LCP.

In some cases, portions of devices described herein may be sandblasted, beadblasted, sodium bicarbonate-blasted, electropolished, etc. In some cases, portions of devices described herein may include a lubricious, hydrophilic, protective, or other type of coating. Hydrophobic coatings such as fluoropolymers provide a dry lubricity which improves guidewire handling and device exchanges. Lubricious coatings improve steerability and improve lesion crossing capability. Suitable lubricious polymers are well known in the art and may include silicone and the like, hydrophilic polymers such as high-density polyethylene (HDPE), polytetrafluoroethylene (PTFE), polyarylene oxides, polyvinylpyrrolidones, polyvinylalcohols, hydroxy alkyl cellulosics, algins, saccharides, caprolactones, and the like, and mixtures and combinations thereof. Hydrophilic polymers may be blended among themselves or with formulated amounts of water insoluble compounds (including some polymers) to yield coatings with suitable lubricity, bonding, and solubility. Some other examples of such coatings and materials and methods used to create such coatings can be found in U.S. Pat. Nos. 6,139,510 and 5,772,609, which are incorporated herein by reference.

It should be understood that this disclosure is, in many respects, only illustrative. Changes may be made in details, particularly in matters of shape, size, and arrangement of steps without exceeding the scope of the disclosure. This may include, to the extent that it is appropriate, the use of any of the features of one example embodiment being used in other embodiments.

What is claimed is:

1. A leadless cardiac pacemaker (LCP) configured for atrial placement in a patient's heart, the LCP comprising:
   a housing;
   two or more electrodes;
   a controller disposed within the housing and operably coupled to the two or more electrodes, the controller configured to sense activation of the atrium of the patient's heart via two or more of the electrodes, and in response, wait for a period time after the sensed activation of the atrium before delivering a pacing pulse via two or more of the electrodes to activate a ventricle of the patient's heart by activating the bundle of His in the patient's atrioventricular septum;
   a rechargeable power supply disposed within the housing and operably coupled to the controller, the rechargeable power supply configured to supply power to the controller;
   a loop structure extending from the housing and convertible between a collapsed configuration for delivery and an expanded configuration for deployment in which the housing fit within the atrium of the patient's heart; and the loop structure is configured as a loop antenna having two or more windings for receiving transmitted energy, the loop structure configured to fit within and extend along the tricuspid valve annulus of the patient's heart;

the controller is further configured to utilize the received transmitted energy to recharge the rechargeable power supply.

2. The LCP of claim 1, further comprising one or more fixation elements secured relative to the housing, the one or more fixation elements configured to fix the LCP relative to the tricuspid valve.

3. The LCP of claim 1, wherein the loop structure comprises one or more fixation features for anchoring the loop structure relative in the tricuspid valve annulus.

4. The LCP of claim 1, wherein the loop structure further comprises a surface treatment configured to encourage endothelialization.

5. The LCP of claim 1, wherein the loop structure comprises a support structure for supporting the two or more windings, wherein the support structure includes a shape memory alloy.

6. The LCP of claim 1, wherein the LCP is configured for deployment within a right atrium of the patient's heart and to deliver a pacing pulse to activate the bundle of His in the patient's atrioventricular septum.

7. A leadless cardiac pacemaker (LCP) configured for atrial placement in a patient's tricuspid valve annulus and provide ventricle pacing via the patient's bundle of His, the LCP comprising:

a housing configured for deployment within the right atrium of the patient's heart;

an energy receiving antenna comprising a loop structure secured relative to the housing, the loop structure convertible between a collapsed configuration for delivery and an expanded configuration for deployment in which the loop structure forms an annulus that is configured to fit within and extend along about the tricuspid valve annulus to help secure the LCP in position relative to the tricuspid valve;

a rechargeable power supply disposed within the housing;

two or more electrodes;

a controller disposed within the housing and operably coupled to the energy receiving antenna, the rechargeable power supply and the two or more electrodes, the controller configured to:

sense atrial electrical activity via two or more of the electrodes;

provide ventricle pacing by delivering pacing pulses via two or more of the electrodes at an energy level that is sufficient to activate the patient's bundle of His; and utilize energy received via the energy receiving antenna to recharge the rechargeable power supply.

8. The LCP of claim 7, wherein the loop structure of the energy receiving antenna comprises a shape memory material.

9. The LCP of claim 7, further comprising one or more fixation elements secured relative to the housing, the one or more fixation elements configured for fixation of the LCP relative to the tricuspid valve.

10. The LCP of claim 7, wherein the energy receiving antenna comprises one or more fixation features for anchoring the energy receiving antenna within the tricuspid valve annulus.

11. The LCP of claim 7, wherein the energy receiving antenna comprises a plurality of wire windings suitable for receiving energy.

12. The LCP of claim 7, wherein the energy receiving antenna further comprises a surface treatment to influence endothelialization.

13. A leadless cardiac pacemaker (LCP) configured for atrial placement, the LCP comprising:

a housing;

two or more electrodes;

a controller disposed within the housing and operably coupled to the two or more electrodes;

a rechargeable power supply disposed within the housing and operably coupled to the controller, the rechargeable power supply configured to supply power to the controller;

a loop structure extending from the housing and convertible between a collapsed configuration for delivery and an expanded configuration for deployment in which the loop structure forms an annulus that is configured to fit within and extend along the tricuspid valve annulus to help secure the LCP in position relative to the tricuspid valve, wherein the loop structure is configured as a loop antenna having two or more windings for receiving transmitted energy;

the controller configured to:

sense activation of the atrium of the patient's heart via two or more of the electrodes;

deliver pacing therapy via two or more of the electrodes to a ventricle of the patient's heart by pacing the bundle of His in the patient's atrioventricular septum; and utilize the received transmitted energy to recharge the rechargeable power supply.

14. The LCP of claim 13, further comprising one or more fixation elements secured relative to the housing, the one or more fixation elements configured to fix the LCP relative to the tricuspid valve of the patient.

15. The LCP of claim 13, wherein the controller is configured to deliver pacing therapy by delivering pacing pulses at an energy level that is sufficient to activate the patient's bundle of His.

16. The LCP of claim 13, wherein the loop structure comprises one or more fixation features for anchoring the loop structure within the tricuspid valve annulus.

17. The LCP of claim 13, wherein the loop structure comprises a support structure for supporting the two or more windings, wherein the support structure includes a shape memory alloy.

* * * * *